United States Patent
Kelly et al.

(10) Patent No.: US 6,849,454 B2
(45) Date of Patent: Feb. 1, 2005

(54) HIGHLY EFFICIENT GENE TRANSFER INTO HUMAN REPOPULATING STEM CELLS BY RD114 PSEUDOTYPED RETROVIRAL VECTOR PARTICLES

(75) Inventors: Patrick F. Kelly, Cincinatti, OH (US); Elio F. Vanin, Houston, TX (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 09/801,302

(22) Filed: Mar. 7, 2001

(65) Prior Publication Data

US 2001/0051375 A1 Dec. 13, 2001

Related U.S. Application Data

(60) Provisional application No. 60/187,534, filed on Mar. 7, 2000.

(51) Int. Cl.$^7$ .......................... C12N 15/09; C12N 7/00; C12N 15/85
(52) U.S. Cl. ..................... 435/455; 435/235.1; 435/325
(58) Field of Search ................................ 435/455, 325, 435/235.1, 320.1

(56) References Cited

U.S. PATENT DOCUMENTS

| | | | |
|---|---|---|---|
| 4,861,719 A | 8/1989 | Miller | 435/236 |
| 5,667,998 A | 9/1997 | Dougherty et al. | 435/172.3 |
| 5,910,434 A | 6/1999 | Rigg et al. | 435/172.3 |
| 5,952,225 A | 9/1999 | Pensiero et al. | 435/352 |
| 6,017,761 A | 1/2000 | Rigg et al. | 435/455 |

FOREIGN PATENT DOCUMENTS

| | | | | |
|---|---|---|---|---|
| WO | WO 9604934 | 2/1996 | ........... | A61K/48/00 |
| WO | PCT/GB96/02061 | 8/1996 | | |
| WO | WO 99/15684 | 4/1999 | ........... | C12N/15/86 |
| WO | WO 9932646 | 7/1999 | ........... | C12N/15/86 |

OTHER PUBLICATIONS

Hennemann et al. Optimization of retroviral–miediated gene transfer to hmuan NOD/SCID mouse repopulating cord blood cells through a systematic analysis of protocol variables. Experimental Hematology, 1999. vol. 27, 817425.*
Onodera et al., Development of improved adenosine deaminase retroviral vectors, 1998, Journal of Virology, pp. 1769–1774.*
Hanenberg et al., Colocalization of retrovirus and target cells on specific fibronectin fragments increase genetic transduction of mammalian cells, 1996, Nature Medicine, vol. 2, pp. 876–882.*
Moritz et al., Fibronectin improves transduction of reconstituting hematopoietic stem cells by retroviral vectors: Evidence of direct viral binding to chymotryptic carboxy--terminal fragments, 1996, Blood, vol. 88, pp. 855–862.*

Porter et al., Comparison of efficiency of infection of human gene therapy target cells via four different retroviral receptors, 1996, Human Gene Therapy, vol. 9, pp. 913–919.*
Uchida et al., HIV, but not murine leukemia virus, vectors mediate high efficiency gene transfer into freshly isolated G0/G1 human hematopoietic stem cells, 1998, Proc. Natl. Acad. Sci. USA, vol. 95, pp. 11939–11944.*
Rebel et al., One–day ex vivo culture allows effective gene transfer into human nonobese diabetic/severe combined immune–deficient repopulating cells using high–titer vesicular stomatitis G protein pseudotyped retrovirus, 1999, Blood, vol. 93, pp. 2217–222.*
Moritz et al., Fibronectin improves transduction of reconstituting hematopoietic stem cells by retroviral vectors: Eveidence of direct viral binding to chymotryptic carboxy-terminal fragments, 1996, Blood, vol. 88, pp. 855–862.*
Uchida et al., HIV, but not murine leukemia virus, vectors mediate high efficiency gene transfer into freshly isolated G0/G1 human hematopoietic stem cells, 1998, Proc. Natl. Acad. Sci. USA, vol. 95, pp. 11939–11944.*
Porter et al., Comparison of efficiency of infection of human gene therapy target cells via four different retroviral receptors, 1996, Human Gene Therapy, vol. 7, pp. 913–919.*
Kelly. P. et al.: "Efficient transducticn of CD34+ and CD38– human haematopoietic cells with SCID repopulating cells (SRC) potential with an oncoretroviral virus (RD114) enevlope protein" Blood, vol. 94, No.10 Part 1 Supl.1, Nov. 15, 1999, p. 611a; Abs. 2718, XP002190046.
Hanenberg, H et al.: "Optimization of Fibronectin–Assisted Retroviral Gene Transfer Into Human CD34 + Hematopoietic Cells" Human Gene Therapy, vol. 8, No. 18, Dec. 10, 1997, pp. 2193–2206, XP000867308.

(List continued on next page.)

Primary Examiner—Anne-Marie Falk
Assistant Examiner—Celine Qian
(74) Attorney, Agent, or Firm—Darby & Darby

(57) ABSTRACT

The present invention pertains to a method for efficiently introducing exogenous genes into stem cells, particularly human stem cells. The method optionally includes the steps of inducing the proliferation of target cells by pre-stimulation with cytokines and/or growth factors, followed by incubating these cells with RD114-pseudotyped vector particles. In a specific embodiment, the vector particles are retronectin-immobilized or ultracentrifugation-concentrated retroviral vector particles pseudotyped with the feline endogenous retrovirus (RD114) envelope protein. The present invention further discloses a method for somatic gene therapy, which can be used for various therapeutic applications and involves introducing a gene of interest contained within the retroviral genome into human repopulating stem cells followed by introducing these cells into a human host. Finally, the present invention discloses a method for monitoring the efficiency of the stem cell-mediated gene transfer based on detecting the presence of the genes (or the expression products) of the retroviral vector in various stem cell-derived lineages of the host.

14 Claims, No Drawings

OTHER PUBLICATIONS

Kelly, P. et al.: "Highly efficient gene transfer into cord blood nonobese diabetic/serve combined immunodeficiency repopulating cells by oncoretroviral vector particles psuedotyped with the feline endogenous retrovirus (RD114) envelope protein" Blood, vol. 96, No. 4 Aug. 15, 2000, pp. 1206–1214, XP002190047.

Hanawa, H. et al.: "Improved transduction of human primitive hematopoietic cells with a lentiviral vector pseudotyped with the envelope protein of endogenous feline leukemia virus (RD114)" Blood, vol. 96, No. 11 Part.1, Nov. 16, 2000, p. 524a, XP002190048.

*An Improved Method For Generating Retroviral Producer Clones For Vectors Lacking A Selectable Marker Gene,* Derek A. Persons et al., Blood Cells, Mole–cules & Diseases (1998) Vol. 24, pp. 167–182.

*High–Titer Packaging Celis Producing Recombinant Retroviruses Resistant to Human Serum,* Cosset, Françis–Loic Cosset et al., Journal of Virology, Dec. 1995, vol. 69, No. 12, pp. 7430–7436.

*A Stable Human–Derived Packaging Cell Line For Production Of High Titer Retrovirus/–Vesicular Stomatitis Viru G Pseudotypes,* Daniel S. Ory, Proc. Natl. Acad. Sci. USA, Oct. 1996, Vol. 93, pp. 11400–11406.

*The RD114/Simian Type D. Retrovirus Receptor Is A Neutral Amino Acid Transporter,* John E. J. Rasko et al., Pro. Natl. Acad. Sci, USA, Mar. 1999, Vol. 96, pp. 2129–2134.

*Envelope–Binding Domain In The Cationic Amino Acid Transporter Determines The Host Range Of Ecotropic Murine Retroviruses–* Lorraine M. Aibritton et al., Journal of Virology, Apr. 1993 p2091–2096 vol. 67, No. 4; © 1993 American Society of Microbiology.

*Improved Transfer of the Leukocyte Integrin CD18 Subunit Into Hematopoietic Cell Lines by Using Retroviral Vectors Having a Gibbon Ape Leukemia Virus Envelope—*Thomas R. Bauer Jr. et al., Blood, Vol. 86 No. 6, Sep. 15, 1995; pp 2379–2387; © 1995 The American Society of Hematology.

*Restoration of Lymphocyte Function In Janus Kinase 3–Deficient Mice By Retroviral–Mediated Gene Transfer—*Kevin D. Bunting et al., Nature Medicine, vol. 4, No. 1, Jan. 1998.

*Lymphocytes As Cellular Vehicles For Gene Therapy In Mouse And Man—*Kenneth Culver et al., Pro. Natl. Acad. Sci. USA, vol. 88, No. 8, pp. 3155–3159, Apr. 15, 1991 Medical Sciences.

*Efficient Transduction of Human Lymphocytes and $CD34^+$ Cells Via Human Immunodefi–ciency Virus–Based Gene Transfer Vectors—*Janet Douglas et al., Human Gene Therapy Vol. 10, No. 6, pp935–945; Apr. 10, 1999.

*Retrovirally Marked CD34–Enriched Peripheral Blood and Bone Marrow Cells Contribute To Long–Term Engraftment After Autologous Transplantation—*Cynthia E. Dunbar et al., Blood, Vol. 85, No. 11, pp 3048–3057, Jun. 1, 1995.

*Human Cord Blood $CD34^+CD38^-$Cell Transduction Via Lentivirus–Based Gene Transfer Vectors—*Jay T. Evans et al., Human Gene Therapy, Vol. 10, No. 9, pp1479–1489, Jun. 10, 1999.

*Extended Long–Term Culture Reveals A Highly Quiescent And Primitive Human Hemato–poietic ProgenitorPopulation—*Quin–Lin Hao et al., Blood, vol. 88, No. 9, pp3306–3313, Nov. 1, 1996.

*Optimization Of Retroviral–Mediated Gene Transfer To Human NOD/SCID Mouse Repopulat–ing Cord Blood Cells Through A Systematic Analysis Of Protocol Variables—*Burkhard Hennemann et al., Experimental Hematology vol. 27, pp. 817–825, Jan. 1999, © 1999 International Society For Experimental Hematology.

*Human Gene Transfer: Characterization of Human Tumor–Infiltrating Lymphocytes As Vehicles For Retroviral–Mediated Gene Transfer In Man—*Attan Kasid et al., Proc. Natl. Acad. Sci. USA, vol. 87, No. 1, pp. 473–477, Jan. 1990.

*Efficient Transduction By An Amphotropic Retrovirus Vector Is Dependent On High–Level Expression Of The Cell Surface Virus Receptor—*Peter Kurre et al., Journal of Virology, vol. 73, No. 1, pp. 495–500, Jan. 1999.

*Retrovirus–Mediated Gene Transfer Into Human $CD34^+$ $38^{Low}$ Primitive Cells Capable Of Reconstituting LongTerm Cultures In Vitro and Nonobese Diabetic–Severe Combined Immunodeficiency Mice In Vivo—*Aliette Marandin et al., Human Gene Therapy, vol. 9, No. 10, pp. 1497–1511, Jul. 1, 1998.

*Construction and Properties of Retrovirus Packaging Cells Based On Gibbon Ape Leukemia Virus—*A. Dusty Miller et al., Journal of Virology, Vol. 65, No. 5, pp. 2220–2224, May 1991, © 1991, American Society For Micro–biology.

*Gene Transfer By Retrovirus Vectors Occurs Only In Cells That Are Actively Replicating At The Time Of Infection—*Daniel G. Miller et al., Molecular and Cellu–lar Biology, vol. 10, No. pp. 4239–4242, Aug. 1990, © 1990 American Society For Microbiology.

*Redesign of Retrovirus Packaging Cell Lines To Avoid Recombination Leading To Helper Virus Production—*A. Dusty Miller et al., Molecular and Cellular Biology, vol. 6, No. 8, pp. 2895–2902, Aug. 1986, © 1986 American Society For Microbiology.

*The Level Of mRNA Encoding The Amphotropic Retrovirus Receptor In Mouse and Human Hematopoietic Stem Cells Is Low And Correlates With The Efficiency Of Retrovirus Transduc–tion,* Donald Orlic et al., Proc. Natl. Acad. Sci. USA, vol. 93, No. 20, pp. 11097–11102, Oct. 1, 1996.

*Comparison Of Efficiency Of Infection Of Human Gene Therapy Target Cell Via Four Different Retroviral Receptors—*Colin D. Porter et al., Human Gene Therapy, vol. 7, No. 8, pp. 913–919, May 20, 1996.

*No Discrepancy Between In Vivo Gene Marking Efficiency Assessed In Peripheral Blood Populations Compared With Bone Marrow Progenitors of $CD34^+$ Cells—*Stephanie E. Sellers, vol. 10, No. 4, pp. 633–640, Mar. 1, 1999.

*Interaction of Vesicular Stomatitis Virus–G Pseudotyped Retrovirus With $CD34^+$ And $CD34^+CD38-$ Hematopoietic Progenitor Cells—*Am Sinclar et al., Gene Ther–apy, vol. 4, pp. 918–927 (1997) © 1997 Stockton Press.

*Receptor Interference Groups Of 20 Retroviruses Plating On Human Cells—*Maja A. Sommerfelt et al., Virology, vol. 176, No. 1, May 1990, © 1990 By Academic Press, Inc.

*Circulating T And B Lymphocytes Of The Mouse I. Migratory Properties—*J. Sprent, Cellular Immunology, Vol. 6, No. 3, Mar. 1973, © 1973 By Aca–demic Press, Inc.

*Differences In The Migration Of B and T Lymphocytes: Organ–Selective Localization In Vivo And The Role Of Lymphocyte–Endothelial Cell Recognition—*Susan K. Stevens et al., The Journal of Immunology, Vvol. 128, No. 2 pp. 844–851, Feb. 1982, © 1982 The American Association of Immunologies.

*Ex Vivo Expansion Of Genetically Marked Rhesus Peripheral Blood Progenitor Cells Results In Diminished Long-Term Repopulating Ability*—J.F. Tisdale, Blood, vol. 92, No. 4, pp. 1131–1141, Aug. 15, 1998.

*In Vivo Selection Of Retrovirally Transduced Hematopoietic Stem Cells*—James A. Allay et al., Nature Medicine, vol. 4, No. 10, pp.1136–1143, Oct. 1998

*Use Of The Green Fluorescent Protein As A Marker To Identify And Track Genetically Modified Hematopoietic Cells*—Derek A. Persons et al., Nature Medi–cine, vol. 4, No. 10, pp. 1201–1205, Oct. 1998.

*Efficient Retroviral –Mediated Gene Transfer To Human Cord Blood Stem Cells With In Vivo Repopulating Potential*—E. Conneally et al., Blood, vol. 91, No. 9, pp. 3487–3493, May 1, 1998.

*Direct Evidence For Multiple Self–Renewal Divisions Of Human In Vivo Repopulating Hematopoietic Cells In Short-Term Culture*—H. Glimm et al., Blood, vol. 94, No. 7, pp. 2161–2168, Oct. 1, 1999, The Journal of The American Society of Hematology.

*Improved Gene Transfer Into Baboon Marrow Repopulating Cells Usihng Recombinant Human Fibronectin Fragment CH–296 In Combination With Interleukin–6, Stem Cell Factor, FLT–3 Ligand, And Megakaryocyte Growth And Development Factor*—Hans–Peter Kiem et al., Blood, vol. 92, No. 6, pp. 1878–1886, Sept. 15, 1998.

*One–Day Ex Vivo Culture Allows Effective Gene Transfer Into Human Nonobese Dia–betic/Severe Combined Immune–Deficient Repopulating Cells Using High–Titer Vesicular Stomatitis Virus G. Protein Pseudotyped Retrovirus*—Vivienne I. Rebel et al., Blood, vol. 93, No. 7, pp. 2217–2224, Apr. 1, 1999, © 1999 The American Society of Hematology.

*High Efficiency Gene Transfer To Human Hematopoietic SCID–Repopulating Cells Under Serum–Free Conditions*—Andrea J. Schilz et al., Blood, vol. 9, pp. 3163–3171; Nov. 1, 1998, © 1998 The American Society of Hematology.

*Highly Efficient Transduction Of The Green Fluorescent Protein Gene In Human Umbilical Cord Blood Stem Cells Capable Of Cobblestone Formation In Long–Term Cultures And Multilineage Engraftment Of Immunodeficient Mice*—Paul B. van Hennik et al., Blood, vol. 92, No. 11, pp. 4013–4022, Dec. 1, 1998, © 1998 The American Society of Hematology.

*Retroviral Marking Of Canine Bone Marrow: Long Term, High–Level Expression Of Human Interleukin–2 Receptor Common Gamma Chain In Canine Lymphocytes*—Todd Whitwam, Blood, vol. 92, No. 5, pp. 1565–1575, Sep. 1, 1998.

*Quantitative Analysis Reveals Expansion of Human Hematopoietic Repopulating Cells After Short–Term Ex Vivo Culture*—Mickie Bhatia et al, J. Exp. Med., vol. 186, No. 4, pp. 619–624, Aug. 8, 1997.

*Stable Transduction of Quiescent $CD34^+CD38^-$ Human Hematopoietic Cells By HIV–1–Based Lentiviral Vectors*—Scott S. Case et al., Proc. Natl. Acad. Sci. USA, vol. 96, pp. 2988–2993, Mar. 1999.

*Transduction Of Human $CD34^+$ Cells That Mediate Long-Term Engraftment Of NOD/SCID Mice By HIV Vectors*—Hiroyuki Miyoshi et al., Science Magazine, vol. 283, pp. 682–686, Jan. 29, 1999.

*High Levels Of Lymphoid Expression Of Enhanced Green Fluorescent Protein In Nonhuman Primates Transplanted With Cytokine–Mobilized Peripheral Blood $CD34^+$ Cell*—Robert E. Donahue et al., Blood, vol. 95, No. 2, pp. 445–452, Jan. 15, 2000 © 2000 The American Society of Hematology.

* cited by examiner

HIGHLY EFFICIENT GENE TRANSFER INTO HUMAN REPOPULATING STEM CELLS BY RD114 PSEUDOTYPED RETROVIRAL VECTOR PARTICLES

This application claims priority under 35 U.S.C. §119(e) of provisional patent application Ser. No. 60/187,534, filed Mar. 7, 2000, which is incorporated herein by reference in its entirety.

The research leading to the present invention was supported in part by National Institutes of Health Grant P01 HL 53749. The United States Government may herein certain rights in the invention.

FIELD OF THE INVENTION

The present invention relates to a method for efficiently introducing exogenous genes into stem cells, particularly human repopulating stem cells, using retroviral vector particles pseudotyped with the feline endogenous retrovirus (RD114) envelope protein. The gene transfer method of the present invention is important for somatic cell gene therapy, for studying the differentiation of various cell lineages, and for creating animal models of various human stem cell conditions.

BACKGROUND OF THE INVENTION

Use of Retroviral Vectors for Gene Therapy

Gene therapy is a novel method under investigation for the treatment of genetic, metabolic and neurologic diseases, cancer and AIDS. The primary goal of gene therapy is to deliver a specific gene to a predetermined target cell, and to direct expression of such a gene in a manner which will result in a therapeutic effect.

Compared to more traditional methods of gene transfer, retroviral vectors are extraordinarily efficient gene delivery vehicles (for reviews see Vile et al., Br. Med. Bull. 1995, 51:12–30; Klimatcheva et al., Front Biosci., 1999, 4:D481–96). The retroviral genome becomes integrated into lost chromosomal DNA, ensuring its long-term persistence and stable transmission to all future progeny of the transduced cell and making retroviral vector suitable for permanent genetic modification. Up to 8 kilobases of foreign gene sequence can be packaged in a retroviral vector particles, which is more than enough for most gene therapy applications. The ability of retroviral vector particles to cause no detectable harm while entering their target cells represents another therapeutically important property. Indeed, there have been no reported short- or long-term toxicity problems associated with the use of the retroviral vectors in human gene therapy trials, now dating back to 1989. In addition, these vectors can be manufactured in large quantities, which allows their standardization and use in pharmaceutical preparations.

In view of the properties described above, it is not surprising that retroviral vectors have been selected as the vectors of choice in about 80% of the clinical gene therapy trials that have been approved to date. The most successful of these clinical experiments have used T cell-directed retroviral vector-mediated gene transfer to cure a severe combined immunodeficiency (SCID) caused by adenosine deaminase (ADA) deficiency (genetic disease) in humans (for review see Onodera et al., Acta Haematol., 1999, 101:89–96).

Most of the commonly used retroviral vectors are of oncoviral origin. These vectors require cell division in order to achieve genome integration and long-term gene expression. Accordingly, lentiviral vectors (e.g., HIV-based), which are retroviruses capable of productively infecting non-dividing cells, have been suggested as an alternative approach to successful gene transfer in quiescent somatic cells (Miller et al., 1990, Mol. Cell Biol., 10:4239–4242; Klimatcheva et al., supra).

Retrovirus vectors. Introduction of genes into host animals is described in U.S. Pat. No. 5,399,346; Mann et al., Cell, 1983, 33:153; U.S. Pat. Nos. 4,650,764 and 4,980,289; Markowitz et al., J. Virol., 1988, 62:1120; U.S. Pat. No. 5,124,263; European Publication Nos. EP 453 242 and EP 178 220; Bernstein et al., Genet. Eng.,1985, 7:235; McCormick, BioTechnology, 1985, 3:689; PCT Publication No. WO 95/07358; and Kuo et al., Blood, 1993, 82:845. Retroviral vectors can be constructed from different types of retrovirus, such as HIV (human immunodeficiency virus), MoMuLV ("murine Moloney leukemia virus"), MSV ("murine Moloney sarcoma virus"), HaSV ("Harvey sarcoma virus"); SNV ("spleen necrosis virus"); RSV ("Rous sarcoma virus"), and Friend virus. In the last decade, several retroviral vector systems, derived from chicken or murine retroviruses, have been developed for the expression of various genes (for reviews see Temin, 1987; Gilboa, 1990; Robbins and Ghivizzani, Pharmacol. Ther., 1998, 80:35–47). The majority of existing gene therapy protocols use simple retroviral vectors based on Murine Leukemia Virus (MLV). These vectors are able to infect many different cell types, and their retroviral promoter, which is often used to control the expression of a heterologous (therapeutic) gene, is active in a wide range of different cell types.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are manipulated to destroy the viral packaging signal from the genes encoding viral structural proteins, retaining the structural genes required to package the co-introduced virus engineered to contain the heterologous gene and the packaging signals. Thus, the viral particles that are produced are not capable of producing additional virus.

Packaging cell lines contain the genes for retrovirus replication and assembly, e.g., gag, pot, and/or env. When transfected with a retroviral genome containing a gene of interest and assembly signals, the packaging cells become producer cells. Suitable packaging cell lines have been described in the prior art, in particular the cell line PA317 (U.S. Pat. No. 4,861,719); the PsiCRIP cell line (PCT Publication No. WO 90/02806) and the GP+envAm-12 cell line (PCT Publication No. WO 89/07150). In addition, the recombinant retroviral vectors can contain modifications within the LTRs for suppressing transcriptional activity as well as extensive encapsidation sequences which may include a part of the gag gene (Bender et al, J. Virol., 1987, 61:1639). Recombinant retroviral vectors are purified by standard techniques known to those having ordinary skill in the art.

Lentivirus vectors. Lentiviral vectors, which are a particular type of retrovirus vector, have also been used as agents for the direct delivery and sustained expression of a transgene in several tissue types,. including brain, retina, muscle, liver, and blood. The vectors can efficiently transduce dividing and nondividing cells in these tissues, and maintain long-term expression of the gene of interest. For a review, see Naldini (Curr. Opin. Biotechnol., 1998, 9:457–63; see also Zufferey, et al., J. Virol., 1998, 72:9873–80). Lentiviral packaging cell lines are available and known generally in the art. They facilitate the production of high-titer lentivirus vectors for gene therapy. An example is a tetracycline-inducible VSV-G pseudotyped lentivirus packaging cell line that can generate virus particles at titers greater than $10^6$ IU/ml for at least 3 to 4 days (Kafri, et al., J. Virol., 1999, 73: 576–584). The vector produced by the inducible cell line can be concentrated as needed for efficiently transducing non-dividing cells in vitro and in vivo.

However, despite this impressive record, there is still a great need for the development of new, improved retroviral vectors and packaging systems to fuel further advances in the field of human gene therapy.

Structure of a Retroviral Vector

Retroviral vectors are infection-competent viral particles that contain functional packaging signals and a crippled genome in which most or all of the retroviral protein coding sequences have been replaced with the gene(s) of interest. As a result, upon infection of a target cell, such viruses cannot undergo more than one round of replication in the absence of a helper virus. Retroviral vector particles are produced by helper cells (also called producer cells), which contain constructs expressing all retroviral proteins necessary for particle production and replication (i.e., at least three proteins: gag, pol, and env). After the introduction (transfection) of the RNA genome of a retroviral vector into such helper cells, it becomes encapsulated into virus particles (due to the presence of specific packaging signals in its RNA) having a complete set of retroviral proteins sufficient to support infection and a single round of replication and carrying a genome containing gene(s) of interest, and the packaging signals required to incorporate the genome into the viral particle. Upon their release from the helper cells, the retroviral vector particles can be isolated from the culture medium and used to infect (transduce) various types of target cells. Following transduction, the RNA genome is reverse transcribed into DNA and the DNA copy (provirus) is integrated into the host genome.

Safe and efficient retroviral-mediated gene transfer systems that are suitable for somatic gene therapy are likely to involve the development of alternative, cell type-targeted vectors containing the cell type-specific retroviral envelope protein (env), which, together with the availability of its cognate receptor, determines infectivity. Cell type targeting may be also achieved by using cell-specific promoters to limit the induction of expression of retroviral vector-encoded genes (for review see Gunzburg et al., Cytokines Mol. Ther., 1996, 2:177–84).

Use of Stem Cells for Retrovirus-Mediated Gene Delivery

The potential use of gene-modified repopulating stem cells as vehicles for retrovirus-mediated gene delivery was first illustrated by the demonstration that hematopoietic systems of lethally irradiated mice can be reconstituted with retroviral vector-transduced syngenic bone marrow cells, and that these cells can, in turn, provide genetically marked progeny, which persist in blood and marrow over extended periods of time (Chu et al, J. Mol. Med., 1998, 76:184–92; Medin and Karlsson, Immunotechnology, 1997, 3:3–19).

The ability to transfer genes into stem cells of hematopoietic, neural or muscular origin would provide an opportunity for somatic gene therapy of various malignant and non-malignant disorders. Thus, gene transfer to primary hematopoietic cells may be used to treat diseases that affect bone marrow and peripheral blood function (for reviews see Anderson, Science, 1984, 226:401–409; Sorrentino et al, pp. 351–426, In: The Development of Gene Therapy, T. Friedmann ed., New York: Cold Spring Harbor Laboratory Press, 1999). Examples of genetic diseases which are potentially curable by transgene-mediated delivery of a normal gene product include: X-linked agammaglobulinemia (Vetrie et al., Nature, 1993, 361:226; Tusukada et al., Cell, 1993, 72:279), ADA deficiency (Anderson, Science, 1992, 256:808), hemophilia (factor VIII and factor IX deficiency) (Miller, Blood, 1990, 76:271; Hoeben et al., Thromb. Haemost., 1992, 67:341; Hoeben et al., Hum. Gene Ther., 1993, 4:179; Herzog and High, Curr. Opin. Hematol., 1998, 5:321–6), and lipoprotein lipase deficiency (Hayden and Ma, Mol. Cell. Biochem., 1992, 113:171; Auwerx et al, Crit. Rev. Clin. Lab. Sci., 1992, 29:243). Indeed, transfer of the gene coding for glucocerebrosidase (GC) via a retroviral vector (MFG-GC) to human CD34 cells obtained from patients with Gaucher's disease was shown to result in correction of the enzyme deficiency in these cells (Barranger et at., Baillieres Clin. Haematol., 1997, 10:765–78). Similarly, hematopoietic stem cells are an attractive target for gene therapy of AIDS because of their ability to generate a broad repertoire of mature T lymphocytes, as well as the monocytic cells (macrophages, dendritic cells and microglia), which are also involved in HIV-1 pathogenesis. A number of synthetic "anti-HIV-1 genes" have been developed which inhibit HIV-1 replication (Engel and Kohn, Front. Biosci., 1999, 4:e26–33). Gene transfer approaches can be also used in diagnosis and treatment of cancer, e.g., to "mark" cancer cells to monitor their persistence in vivo in patients, to protect normal cells from toxic chemotherapeutic agents, to correct a genetic defect in or to confer a novel function on the cancer cell (Clay et al., Pathol. Oncol. Res., 1999, 5:3–15). For example, preliminary experiments in transgenic mice have demonstrated that overexpression of the human multidrug resistance 1 (MDR1) gene results in a complete protection against high doses of cytostatic drugs (Fruehauf et al., Recent Results Cancer Res., 1998, 144:93–115).

Several gene therapy protocols involving retroviral-vector-mediated transfer of exogenous genes into cells of hematopoietic lineage are in clinical trials. These include the introduction of the adenosine deaminase (ADA) gene into peripheral blood T cells of ADA deficient, severe combined immunodeficiency (SCID) patients (Sprent, Cell. Immunol., 1983, 7: 10; Stevens et al., J. Immunol., 1982, 128:844), and the introduction of marker genes or lymphokine genes into tumor infiltrating (TIL) T cells (Kasis et al., Proc. Natl. Acad. Sci. USA, 1990, 87:473; Culver et al., 1991, ibid., 88:3155).

Existing Problems in Retroviral-Mediated Gene Transfer to Stem Cells

Extensive efforts have been invested in adapting oncoretroviral vectors for gene transfer into stem cells (Allay et al., Nat. Med., 1998, 4:1136–1143; Bunting et al., Nat. Med., 1998, 4:58–64; Persons et al., Nat. Med, 1998, 4:1201–1205; Donahue et al., Blood, 2000, 95:445–452; Dunbar et al., Blood, 1995, 85:3048–3057; Kiem et al, Blood, 1998, 92:1878–1886). Despite considerable success in murine models, retroviral-mediated gene transfer into human stem cells has been difficult to achieve due to low abundance of viral receptors, inhibition of retroviral transgene expression, and the relative quiescence of the target cell population (Kurre et al., J. Virol., 1990, 73:495–500; Miller et al., Mol. Cell Biol., 1990, 10:4239–4242; Orlic et al., Proc. Natl. Acad. Sci. USA, 1996, 93:11097–11102; Bhatia et al., J. Exp. Med., 1997, 186:619–624; Glimm et al., Blood, 1999, 94:2161–2168; Hao et al., Blood, 1996, 88:3306–3313). As explained above, the latter problem can be solved by the use of lentiviral vectors, which are able to infect non-dividing cells. In addition, the recent evidence suggests that repopulating hematopoietic stem cells can be induced to divide in short-term cultures with high concentrations of cytokines (Bhatia et al., supra; Glimm H, et al., supra), thus opening the possibility to increase the efficiency of oncoviral-mediated transduction. However, upon stimulation these stem cells are likely to differentiate, thus defeating the goal of using them in the first place.

It appears therefore that the retroviral receptor deficiency and the efficiency and persistence of retroviral transgene expression are the major remaining barriers to stem cell-targeted gene transfer.

Another factor which has complicated the development of stem cell-targeted gene therapy approaches for human disorders is the lack of reliable in vitro surrogate assays for the repopulating cells. Thus, successful gene transfer into hematopoietic progenitors, as evaluated in in vitro clonogenic assays, has been a poor predictor of long-term gene transfer into repopulating stem cells in large animal models or human clinical trials (Dunbar et al., supra). Cells capable of initiating long-term culture (LTC-IC), particularly those which give rise to hematopoietic progenitors over 10–12 weeks, may be a much better surrogate for repopulating stem cells (Hao et al., supra; Sutherland et al., Proc. Natl. Acad. Sci. USA,1990, 87:3584–3588). Another surrogate for stem cell targeted gene transfer are the primitive human hematopoietic cells that are able to establish hematopoiesis in immunodeficient mice, such as the non-obese diabetic/ severe combined immunodeficiency (NOD/SCID) mouse strain. Human NOD/SCID repopulating cells (SRC) become engrafted in various hematopoietic cell lineages and can be recovered from murine bone marrow months after transplantation (Kamel-Reid et al., Science, 1988, 242:1706–1709; Vormoor et al., Blood,1994, 83:2489–2497; Cashman et al., Blood, 1997, 89:4307–4316; Larochelle et al., Nat. Med.,1996, 2:1329–1337). It follows that gene transfer strategies resulting in retroviral marking of a significant proportion of the progeny of SRC would be a better predictor for stem cell gene transfer than surrogates evaluated by in vitro assays, (Larochelle et al., Nat. Med., 1996, 2:1329–1337).

Most vector preparations utilized for gene transfer into human cells contain particles having amphotropic specificity based on the structure of their envelope protein. Amphotropic viral particles have a broad host range that includes human cells (Kurre et al., J. Virol.,1999, 73 :495–500). In contrast, ecotropic vector particles used for gene transfer into murine stem cells are unable to transduce human cells because of interspecies polymorphic variation in the cationic transporter which serves as the receptor for ecotropic vector particles (Albritton et al., J. Virol., 1993, 67:2091–2096; Kizhatil et al., J. Virol., 1997, 71:7145–7156). Despite their broad cell type specificity, amphotropic vector particles infect human hematopoietic stem cells very inefficiently. It has been recently demonstrated that amphotropic vector particles enter their target cells via interactions with aphosphate transporter (van Zeijl et al., Proc. Natl. Acad. Sci. USA, 1994, 91:1168–1172; Miller et al., Proc. Natl. Acad. Sci. USA, 1994, 91:78–82; Kavanaugh et al., Proc. Natl. Acad. Sci. USA, 1994, 91:7071–7075), which is expressed at very low levels on primitive human hematopoietic cells (Orlic et al., supra) and possibly other types of stem cells. To overcome this barrier to retroviral-mediated gene transfer, vector preparations pseudotyped with envelope proteins from other viruses have been generated and studied.

Oncoretroviral vectors pseudotyped with the envelope protein of the Gibbon Ape Leukemia Virus (GALV) were shown to transduce human clonogenic hematopoietic progenitor cells (Bauer et al., Blood, 1995, 86:2379–2387) and NOD/SCID repopulating cells (SRC) from cord blood more efficiently than amphotropic vector particles (van Hennik et al., Blood, 1998, 92:4013–4022; Marandin et al, Hum. Gene Ther., 1998, 9:1497–1511; Conneally et al., Blood, 1998, 91:3487–3493). In accord with these data, the GALV receptor, also a phosphate transporter, was found to be expressed at a somewhat higher level than the amphotropic receptor (Kiem et al., Blood, 1998, 92:1878–1886; Bauer et al., Blood, 1995, 86:2379–2387). Thus, in studies in the NOD/SCID model, approximately 25% of human $CD45^+$ cells in multiple hematopoietic lineages of transplant recipients were positive for the vector genome as documented by PCR or transgene expression only after multiple exposures to viral vectors (van Hennik et al., supra; Marandin et al., supra; Schilz et al., Blood, 1998, 92:3163–3171; Hennemann et al., Experimental Hematology,1999, 27:817–825). These data correlate with the results of larger animal studies in which GALV pseudotyped oncoretroviral vector particles show higher frequency of gene transfer than amphotropic vector particles and are incorporated into 10% of myeloablated canine and baboon models (Kiem et al., Blood, 1998, 92:1878–1886; Tisdale et al., Blood, 1998, 92:1131–1141; Sellers et al., Hum. Gene Ther., 1999, 10:633–640; Whitwam et al., Blood, 1998, 92:1565–1575).

The G envelope protein of vesicular stomatitis virus (VSV-G), a rhabdovirus, has been used to pseudotype both lentiviral and oncoviral vector particles (Yang et al., Hum. Gene Ther., 1995, 6:1203–1213; Emi et al., J. Virol., 1991, 65:1202–1207; Friedmann et al., Nat. Med., 1995, 1:275–277; Akkina et al., J. Virol., 1996, 70:2581–2585; Naldini et al., Science, 1996, 272:263–267). The VSV-G pseudotyped particles can be concentrated 100–1,000 fold by centrifugation and they enter target cells via interaction with phospholipids which are found on all cell types (Burns et al., Proc. Natl. Acad. Sci. USA, 1993, 90:8033–8037). It has been shown that both VSV-G pseudotyped oncoviral and lentiviral vector particles efficiently transduce hematopoietic stem cells (Evans et al, Hum. Gene Ther., 1999, 10:1479–1489; Douglas et al, Hum. Gene Ther., 1999, 10:935–945; Case et al., Proc. Natl. Acad. Sci. USA, 1999, 96: 2988–2993; Sinclair et al., Gene Ther., 1997, 4:918–927). Successful gene transfer into SRC using VSV-G pseudotyped oncoretroviral or lentiviral vector particles has been also reported (Rebel et al., Blood, 1999, 93:2217–2224; Miyoshi et al., Science, 1999, 283:682–686). Despite the increased efficiency of gene transfer observed with VSV-G pseudotyped particles compared with GALV pseudotyped and amphotropic vector particles, the use of these particles for therapeutic purposes is questionable. VSV-G protein is toxic to producer cells by causing the membrane fusion, and the inducible promoters must be used to control its expression (Yang et al., supra; Ory et al., Proc. Natl. Acad. Sci. USA, 1996, 93:11400–11406).

Vector particles pseudotyped with the envelope protein of the feline endogenous virus RD114 have been described (U.S. Pat. No. 5,952,225). The RD114 retrovirus is a member of the large interference group 1 of retroviruses all of which use the same receptor on human cells (Sommerfelt et al., Virology, 1990, 176:58–69) recently identified as a neutral amino acid transporter (Rasko et al., Proc. Natl. Acad. Sci. USA, 1999, 96:2129–2134). In addition, murine RD114 pseudotyped vector particles have been shown transduce human hematopoietic cells at about the same efficiency as amphotrophic vector, when the target cells were cultured with the producer cell line (Porter et al, Hum. Gene Ther., 1996, 7:913–919; Rasko et al., Proc. Natl. Acad. Sci. USA, 1999, 96:2129–2134). However, in practice it is highly undesirable to co-culture the target cells with the producer cells as this is not considered a Good Manufacturing Process. Indeed, one cannot regard the results of this experiment with high confidence. Using this approach, the level of transduction was only the same as with amphotropic viral particles, which indicates that the method does not correlate with previously noted in vitro data.

Thus, there is a clear need in the art for more efficient, and thus cost effective, ex vivo transduction of stem cells. There is a further need for ex vivo transduction of stem cells without inducing stem cell differentiation. The present invention advantageously addresses these and other needs in the art.

The citation of any reference herein should not be construed as an admission that such reference is available as prior art to the instant invention.

SUMMARY OF THE INVENTION

The invention provides a highly efficient method for transducing stem cells with a vector particle, particularly a retroviral vector particle, containing a gene of interest, e.g., in a modified retroviral genome. This method comprises contacting target cells with vector particles pseudotyped with feline endogenous virus RD114 envelope protein (including binding fragments and fusion proteins) and containing a gene of interest. A feature of the invention is that the vector particles are substantially free of producer cells and producer cell supernatant. Thus, high efficiency transduction of the invention is consistent with Good Manufacturing Practices and avoids conditions that are likely to induce stem cell differentiation. The advantages of the invention can be achieved by using artificial RD114 pseudotyped particles, by pre-adsorbing the retroviral particles onto a surface that promotes adherence of the retroviral particles, or by freeing the viral particles of producer cells and producer cell supernatant by ultracentrifugation, or both of the latter two.

According to the disclosed method, the target stem cells are pre-stimulated by treatment with signaling molecules selected from the group consisting of cytokines, growth factors and phytohemagglutinin. progenitor cells derived from primitive hematopoietic cells. Such cells can be cord blood cells, mobilized peripheral blood cells, bone marrow cells, and liver cells. Preferably they are CD34$^+$ cells; more preferably they are CD34$^+$,CD38$^-$ cells.

The invention further provides a population of stem cells transduced with vector particles, particularly retroveral vector particles, pseudotyped with feline endogenous virus RD114 envelope protein and containing a gene of interest. The population of stem cells are substantially undifferentiated. Upon engraftment of the transduced stem cells contacted one time with the retroviral particles into a host, greater than 10% of the transduced cells can express the gene of interest. In a more specific embodiment, greater than about 40% of the transduced cells express the gene of interest. These are remarkable results.

In addition, the invention provides a method for introducing a gene of interest into a host. This method comprises introducing the population of transduced stem cells of the invention into a host, e.g., a human (and the stem cells are human stem cells), a non-human host (when the stem cells are autologous or syngenic to the non-human host), or an immunodeficient animal (and the stem cells are human stem cells). Preferably, greater than about 40% of the engrafted transduced stem cells express the gene of interest.

Thus, the invention further provides a non-human animal engrafted with the transduced stem cells of the invention, such as an immunodeficient mouse or a monkey.

The invention further provides a method of treating a disease or disorder, which method comprises administering to a patient a therapeutically effective dose of the population of transduced stem sells of the invention, wherein the gene of interest is a therapeutic gene.

A kit comprising retroviral vector particles pseudotyped with feline endogenous virus RD114 envelope protein and containing a gene of interest their genome pre-adsorbed onto a surface that promotes adherence of the retroviral particles, wherein the retroviral vector particles are substantially free of producer cells and producer cell supernatant, is also provided.

Also, a method for preparing the kit is disclosed. This method comprises contacting the surface with the retroviral vector particles for a sufficient period of time to permit adherence of the retroviral particles to the surface, and removing supernatant in which the retroviral particles were suspended from the surface. The invention advantageously permits storing the retroviral particles adsorbed onto the surface, e.g., at $-70°$ C.

DETAILED DESCRIPTION OF THE INVENTION

The present invention relates to a method for efficiently introducing exogenous genes into stem cells which, in turn, leads to introducing the exogenous genes into cell lineages derived from these stem cells. Moreover, the high efficiency transduction achieved in accordance with this invention can be achieved without inducing stem cell differentiation. The invention is based, in part, on the discovery that RD114 pseudotyped retroviral vectors efficiently transduce hematopoietic stem cells due to unique properties and stability of the vector preparations. These properties include the unexpected ability to highly concentrate RD114 envelope pseudotyped retroviral vectors by adsorbing it on a surface or by ultracentrifugation, thus permitting more effective transduction free of producer cells and producer cell supernatant. Thus, advantages of the present invention are due to the unique, and previously unknown (as well as unexpected) properties of RD114 pseudotyped retroviruses.

The term "vector particle" refers to a retroviral vector particle or an artifical particle, such as a lyposome, protein matrix, or other gene transfer particle (described in greater detail, infra) that contains genetic material for transfer into and expression in a cell. The genetic material can be a modified retroviral genome or a recombinant DNA or RNA construct.

As used herein, "retroviral vector" and "retroviral vector particle" refer to a modified retroviral genome that contains a heterologous or exogenous gene of interest within the retroviral packaging signals, that has been incorporated within a retroviral particle assembled by a producer cell. The retroviral particles of the present invention contain an RD114 envelope (env) protein; thus, they are RD114-pseudotyped retroviral particles.

As one of ordinary skill in the art would appreciate, the term "pseudotyped with feline endogenous virus RD114 envelope protein" means that the vector particle contains an RD114 protein, or the N-terminal segment of the protein involved in binding, so that the vector particle demonstrates binding properties of RD114. The RD114 protein or binding portion can be included in a fusion construct.

By "highly efficient", the present invention contemplates significant improvements over the efficiency of stem cell transduction previously reported. It should be noted that efficiency as used herein refers to transduction of stem cells capable of expressing the transgene (the gene of interest) in vivo; in vitro transduction efficiencies can be very high, for example on the order of 90%. The only level of transduction efficiency that has any relevance is long term marking in hosts, particularly humans and large animals, like the rhesus monkey. However, the highest level of transduction efficiency reported in vivo (i.e., after engraftment of the cells transduced ex vivo), has been reported to be less than 10% per number of exposures to (i.e., times contacted with) transducing retroviral vectors, as discussed above. The best level of transduction efficiency of which the inventors are aware in a relevant model is no more than 10%. In a specific embodiment, the present invention permits transduction efficiency of about 40% after a single transduction step (contacting the target stem cells with the retroviral vector preparation one time). When considered at the level of the best single animal, the prior art has reported 71% engraftment (in mice), compared to the present invention with an efficiency exceeding 90% in individual animals.

High efficiencies of the invention are achieved by contacting the stem cells with retroviral vector particles pre-adsorbed onto a surface. In a preferred embodiment, the single exposure of stem cells to the pre-adsorbed retroviral particles results in very high levels of transduction efficiency. Higher levels still can be achieved by supplying additional retroviral particles. In order to preserve the phenotype of the target stem cells, the amount of producer cell supernatant added with this second exposure to retroviral particles should be minimized. An advantage of the present invention is the discovery that the RD114 env protein permits concentration of the retroviral particles by ultracentrifugation. Thus, a second exposure or contacting step of the stem cells with retroviral particles is preferably achieved with ultracentrifuge-concentrated retroviral particles.

The term "ex vivo" is used herein to refer to transduction of target stem cells with a retroviral vector of the invention in a culture system outside of the host, followed by administration of the transduced stem cells into the host, i.e., engraftment of the transduced stem cells. This term is used in contrast to in vitro, which only refers to transduction and maintenance of target cells in tissue culture, and in vivo, in which the vector is administered to the host animal for transduction of the endogenous cells.

As used herein, the term "stem cells" includes but is not limited to hematopoietic stem cells, neural stem cells, mesenchymal (particularly muscular) stem cells, and liver stem cells. Stem cells are capable of repopulating tissue(s) in vivo. Hematopoietic stem cells are progenitor cells derived from primitive human hematopoietic cells. In a specific embodiment, infra, for gene transfer into hematopoietic stem cells, the target cells are selected from the group consisting of cord blood cells, mobilized peripheral blood cells, bone marrow cells, and liver cells. The cells best able to repopulate hematopoietic tissues are $CD34^+$ cells, and preferably $CD34^+, CD38^-$ cells. "Mesenchymal stem cells" refer to the cells isolated from connective tissue, including muscle and dermis, which have the ability to differentiate into several phenotypes of the mesodermal lineage, including cartilage and bone (see U.S. Pat. Nos. 5,906,934, 5,827,735, and 5,486,359). The term "target" is used to indicate that the retroviral vector is intended to transduce the cells.

A stem cell "population" refers to the stem cells following contact with and transduction by the retroviral vector; because not every stem cell is transduced or transduced effectively (such that it expresses the transgene after engraftment), the cells constitute a heterogeneous population, hence use of that term. While it is possible to isolate or purify the transduced cells (e.g., by including a selection marker in the retroviral vector genome), that is not necessary in the practice of the invention (and, indeed, to the extent that extraneous genes and gene products, including selection genes, are undesirable when the transduced cells are engrafted into a human host for a gene therapy, such markers are preferably avoided).

The novel gene transfer method of the instant invention involves the use of the retroviral vector (also referred to herein as "retroviral vector particles") pseudotype with feline endogenous virus RD114 envelope protein. As disclosed in specific embodiments, these RD114 pseudotyped retroviral vector particles are generated from producer cells which comprise: (i) a polynucleotide encoding a minimal gag-pol open reading frame (ORF) and expressing gag and pol proteins; (ii) a polynucleotide encoding a minimal ORF of feline endogenous virus RD114 envelope protein (env); (iii) a retroviral vector including a 5' LTR, a 3' LTR, a packaging signal, and a gene of interest encoding a protein or polypeptide of interest under control of an appropriate expression control sequence ("vector genome"). It follows that the retroviral vector particles employed in the present invention contain in their genome only the heterologous coding sequences or sequences and the signals needed for particle assembly (packaging). These vectors can efficiently replicate to produce infective virus only in the producer (helper) cells (which supply gag, pol and env proteins), and undergo a single cycle of replication and insertion upon infecting a target cell.

The retroviral vector particles are "substantially free of factors that induce stem cell differentiation" when they are substantially free of producer cells and producer cell supernatant, or when the packaging cells do not themselves produce differentiation factors that affect the stem cells, or when the producer cell culture fluid is treated to neutralize or remove any such factors, e.g., with inhibitory antibodies or by immunoprecipitation. The retroviral vector particles are "substantially free of producer cells and producer cell supernatant" when they have been isolated from the producer cell culture in which they were produced. The term "substantially" with respect to the producer cells means that the presence of producer cells cannot be detected by microscopy, more preferably by immunoassay, more preferably still by nucleic acid hybridization (Northern or Southern hybridization), and most preferably by nucleic acid amplification, e.g., by polymerase chain reaction (PCR). The term substantially with respect to culture fluid means that the amount of differentiation-inducing factor in producer cell culture fluid present is too low to cause the stem cells to differentiate, proliferate, die, or undergo any other undesirable outcome. In a specific embodiment, substantially free of producer cell culture fluid means that, when contacted with the target stem cells, less than about 10% of the culture fluid in which the stem cells are suspended is producer cell culture fluid; preferably less than about 1%; and more preferably less than about 0.1%.

In specific embodiments, the producer cells of the present invention are derived from HT1080 human sarcoma cell line (ATCC CCL-121), 293T human embryonic kidney cell line (ATCC CRL-1573), or NIH 3T3 mouse fibroblast cell line (ATCC CRL-1658), to mention a few possibilities. The retroviral vector particles can be found in the producer cell culture fluid, which is the culture medium in which the producer cells grow and effectively permit retroviral vector replication and production.

According to the invention, the retroviral vector particles can be oncoviral particles or lentiviral particles. In a specific embodiment, the RD114 pseudotyped oncoviral vector genome is derived from murine leukemia virus (MLV). In another specific embodiment, the RD114 pseudotyped oncoviral vector genome is derived from mouse stem cell virus (MSCV). The present invention also discloses the generation of HIV-1-based RD114 pseudotyped lentiviral vector particles. In each of these cases, the key element is using an RD114 env gene in the producer cell.

As used herein, the term "isolated" means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The phrase "pharmaceutically acceptable", whether used in connection with the pharmaceutical compositions of the invention or vaccine compositions of the invention, refers to molecular entities and compositions that are physiologically tolerable and do not typically produce untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18$^{th}$ Edition.

The term "about" or "approximately" will be known to those skilled in the art in light of this disclosure. Generally it means that a particular value can range within an acceptable error for the type of measurement from which the value is obtained. For example, the term can mean within 20%, more preferably within 10%, and more preferably still within 5% of a given value. Alternatively, especially in biological systems, the term "about" preferably means within about a log (i.e., an order of magnitude), preferably within a factor of five and more preferably within a factor of two, of a given value, depending on how quantitative the measurement.

Molecular Biology—Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); DNA Cloning: 55 A *Practical Approach*, Volumes I and II (D. N. Glover ed. 1985); *Oligonucleotide Synthesis* (M. J. Gait ed. 1984); *Nucleic Acid* (D. N. Glover ed. 1985); *Oligonucleotide Synthesis* (M. J. Gait ed. 1984); *Nucleic Acid Hybridization*, B. D. Hames & S. J. Higgins eds. (1985); *Transcription And Translation*, B. D. Hames & S. J. Higgins, eds. (1984); *Animal Cell Culture*, R. I. Freshney, ed. (1986); *Immobilized Cells And Enzymes*, IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994).

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins, and may or may not include regulatory DNA sequences, such as promoter sequences; that determine for example the conditions under which the gene is expressed. The transcribed region of a gene can include 5'- and 3'-untranslated regions (UTRs) and introns in addition to the translated (coding) region. As used herein, the term "gene" in conjunction with a vector means a coding sequence operatively associated with an expression control sequence; it can therefore be an artificial construct.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Promoters that may be used to control gene expression include, but are not limited to, cytomegalovirus (CMV) promoter (U.S. Pat. Nos. 5,385,839 and 5,168,062), the SV40 early promoter region (Benoist and Chambon, Nature, 1981, 290:304–310), the promoter contained in the 3' long terminal repeat of Rous sarcoma virus (Yamamoto, et Natl. Acad. Sci. U.S.A., 1981, 78:1441–1445), the regulatory sequences of the metallothionein gene (Brinster et al, Nature, 1982, 296:39–42); prokaryotic expression vectors such as the β-lactamase promoter (Villa-Komaroff, et al., Proc. Natl. Acad. Sci. U.S.A., 1978, 75:3727–3731), or the tac promoter (DeBoer, et al, Proc. Natl. Acad. Sci. U.S.A., 1983, 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature, 1985, 315:338–340; Kollias et al., 1986, Cell 46:89–94), hematopoietic stem cell differentiation factor promoters, erythropoietin receptor promoter (Maouche et al., Blood, 1991, 15:2557), etc.

A coding sequence is "under the control" of or "operably associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as an mRNA or a protein. The expression product itself, e.g. the resulting mRNA or protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell. "Conditions that permit expression", in vitro are culture conditions of temperature (generally about 37° C.), humidity (humid atmosphere), carbon dioxide concentration to maintain pH (generally about 5% $CO_2$ to about 15% $CO_2$), pH (generally about 7.0 to 8.0, preferably 7.5), and culture fluid components, that depend on host cell type. In vivo, the conditions that permit expression are primarily the health of the animal, which depends on adequate nutrition, water, habitation, and environmental conditions (light-dark cycle, temperature, humidity, noise level). In either system, expression may depend on a repressor or inducer control system, as well known in the art.

The term "transfection" means the introduction of a "foreign" (i.e. extrinsic or extracellular) gene, DNA or RNA sequence into a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transfected" and is a "transfectant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Retroviral vectors typically comprise the RNA of a transmissible agent, into which a heterologous sequence encoding a protein of interest is inserted. Typically, the retroviral RNA genome is expressed from a DNA construct. A common way to insert one segment of DNA into another segment of DNA involves the use of enzymes called restriction enzymes that cleave DNA at specific sites (specific groups of nucleotides) called restriction sites. A "cassette" refers to a DNA segment that can be inserted into a vector or into another piece of DNA at a defined restriction site. Preferably, a cassette is an "expression cassette" in which the DNA is a coding sequence or segment of DNA that codes for an expression product that can be inserted into a vector at defined restriction sites. The cassette restriction sites generally are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of DNA construct is a "plasmid" that generally is a self-contained molecule of double-stranded DNA, usually of bacterial origin, that can readily accept additional (foreign) DNA and which can be readily introduced into a suitable producer cell. A plasmid vector often contains coding DNA and promoter DNA and has one or more restriction sites suitable for inserting foreign DNA. A large number of vectors, including plasmid and fungal vectors, have been described for replication and/or expression in a variety of eukaryotic and prokaryotic hosts. Non-limiting examples include pKK plasmids (Amersham Pharmacia Biotech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. A "retroviral plasmid vector" means a plasmid which includes all or part of a retroviral genome including 5' and 3' retroviral long-term repeat (LTR) sequences, a packaging signal (.psi.), and may include one or more polynucleotides encoding a protein(s) or polypeptide(s) of interest, such as a therapeutic agent or a selectable marker. Such retroviral plasmid vectors are described, e.g., in U.S. Pat. No. 5,952,225 (column 4, line 5 to column 5, line 8), which is specifically incorporated herein by reference.

Synthetic vector particles can be prepared using lipofection technology, optionally with other transfection facilitating agents (peptides, polymers, etc.). Synthetic cationic lipids can be used to prepare liposomes for in vivo transfection of a gene (Felgner, et. al., Proc. Natl. Acad. Sci. USA 1987, 84:7413–7417; Felgner and Ringold, Science 1989, 337:387–388; see Mackey, et al., Proc. Natl. Acad. Sci. USA 1988, 85:8027–8031; Ulmer et al., Science 1993, 259:1745–1748). Useful lipid compounds and compositions for transfer of nucleic acids are described in PCT Publications WO95/18863 and WO96/17823, and in U.S. Pat. No. 5,459,127. Lipids may be chemically coupled to RD114 molecules for the purpose of targeting (see Mackey, et. al., supra), or by insertion of an RD114 polypeptide construct into the lipid bilayer, i.e., by analogy to a transmembrane protein.

The term "host" or "host animal" means any animal that is selected, modified, engrafted, or manipulated in any way, for the production of the protein of interest (expressed by the gene of interest) in the host. Non-human animal hosts can further be used for screening or other assays, as described infra. Human hosts can be used to study the distribution and fate of engrafted stem cells, e.g., carrying a marker gene.

The term "heterologous" refers to a combination of elements not naturally occurring. For example, heterologous DNA refers to DNA not naturally located in the cell, or in a chromosomal site of the cell. A heterologous expression regulatory element is such an element operatively associated with a different gene than the one it is operatively associated with in nature. In the context of the present invention, a coding sequence of interest is heterologous to the retroviral vector RNA in which it is inserted for expression, and it is heterologous to a host cell or animal containing such a vector in which it is expressed, e.g., a CHO cell, a mouse, a monkey, or a human.

A number of selection systems may be used, including but not limited to the herpes simplex virus thyrmidine kinase (Wigler et al., Cell, 1977, 11:223), hypoxanthine-guanine phosphoribosyltransferase (Szybalska & Szybalski, Proc. Natl. Acad. Sci. USA, 1962, 48:2026), and adenine phosphoribosyltransferase (Lowy et al., Cell, 1980, 22:817) genes can be employed in tk-, hgprt-, or aprt-cells, respectively. Also, antimetabolite resistance can be used as the basis of selection for the following genes: dhfr, which confers resistance to methotrexate (Wigler et al., Proc. Natl. Acad. Sci. USA, 1980, 77:3567; O'Hare et al., Proc. Natl. Acad. Sci. USA, 1981, 78:1527); gpt, which confers resistance to mycophenolic acid (Mulligan & Berg, Proc. Natl. Acad. Sci. USA, 1981, 78:2072); neo, which confers resistance to the aminoglycoside G-418 (Colberre-Garapin et al., J. Mol. Biol., 1981, 150:1); and hygro, which confers resistance to hygromycin (Santerre et al., Gene, 1984, 30:147).

One aspect of the invention involves the use of a retroviral vector genome expressing a bicistronic transcript encoding the gene of interest and a selectable marker gene, wherein the selectable marker gene is arranged downstream of the stop codon of the gene of interest and is separated from it by an internal ribosome entry site to insure that it is expressed from the corresponding mRNA as a result of translation reinitiation. According to the invention, the inclusion of a selectable marker gene allows the efficient selection of producer cells and transduced target cells. Thus, in one embodiment, the present invention discloses the use of a selectable marker gene encoding a drug-resistant variant of human dehydrofolate reductase which confers the resistance to trimetrexate. In another embodiment, the present invention discloses the use of retroviral vectors which do not encode a selectable marker, but only the gene(s) of interest.

Use of the Vector Particles

According to the invention, the gene of interest carried by the RD114 can be any gene pseudotyped vector particle. In a preferred embodiment, the gene of interest is a therapeutically relevant gene. The non-limiting examples of such genes include genes encoding wild-type proteins missing in mutant cells (e.g., factors VII and IX, tumor suppressor genes, etc.) and genes involved in drug resistance or anti-viral resistance (e.g., MDR, ribozymes, antisense RNAs, anti-vital proteases, etc.). Examples of therapeutic genes include polynucleotides encoding tumor necrosis factor (TNF) genes, such as TNF-$\alpha$; genes encoding interferons such as Interferon-$\alpha$, Interferon-$\beta$, and Interferon-$\gamma$; genes encoding interleukins such as IL-1, IL-$\beta$, and Interleukins 2 through 14; genes encoding GM-CSF; genes encoding adenosine deaminase, or ADA; genes which encode cellular growth factors, such as lymphokines, which are growth factors for lymphocytes; genes encoding epidermal growth factor (EGF), and keratinocyte growth factor (KGF); genes encoding soluble CD4; Factor VIII; Factor IX; cytochrome b; glucocerebrosidase; T-cell receptors; the LDL receptor, ApoE, ApoC, ApoAI and other genes involved in cholesterol transport and metabolism; the alpha-1 antitrypsin ($\alpha$1 AT) gene; the insulin gene; the hypoxanthine phosphoribosyl transferase gene; the CFTR gene; negative selective markers or "suicide" genes, such as viral thymidine kinase genes, e.g., the Herpes Simplex Virus thymidine kinase gene, the cytomegalovirus virus thymidine kinase gene, and the varicella-zoster virus thymidine kinase gene; Fc receptors for antigen-binding domains of antibodies, antisense sequences which inhibit viral replication, such as antisense sequences which inhibit replication of hepatitis B or hepatitis non-A non-B virus; antisense c-myb oligonucleotides; anti-tumor protein intracellular antibodies; and antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase; tissue plasminogen activator (tPA); urinary plasminogen activator (urokinase); hirudin; the phenylalanine hydroxylase gene; nitric oxide synthesase; vasoactive peptides; angiogenic peptides; the dopamine gene; the nitric oxide synthesase; vasoactive peptides; angiogenic peptides; the dopamine gene; the dystrophin gene; the $\beta$-globin gene; the $\alpha$-globin gene; the HbA gene; protooncogenes such as the ras, src, and bcl genes; tumor-suppressor genes such as p53 and Rb; the LDL receptor; the heregulin-$\alpha$ protein gene, for treating breast, ovarian, gastric and endometrial cancers; monoclonal antibodies specific to epitopes contained within the $\beta$-chain of a T-cell antigen receptor; the multidrug resistance (MDR) gene; polynucleotides encoding ribozymes; antisense polynucleotides; genes encoding secretory peptides which act as competitive inhibitors of angiotensin converting enzyme, of vascular smooth muscle calcium channels, or of adrenergic receptors, and polynucleotides encoding enzymes which break down amyloid plaques within the central nervous system. It is to be understood, however, that the scope of the present invention is not to be limited to any particular therapeutic agent. In one of the embodiments, the invention also discloses the use of a gene of interest encoding a marker gene, such as enhanced green fluorescent protein (EGFP). Such marker genes are particularly useful for tracking the fate of transduced cells, e.g., during clinical development of a gene therapy based on the vectors and methods of the invention.

The present invention also discloses a method for somatic gene therapy which involves introducing a gene of interest contained within the vector particle, such as in a retroviral genome, into human repopulating stem cells followed by introducing these cells into a human host. Such therapies can be tested on the animal models described herein. In accord with the present invention, an animal model system is described for use in retroviral gene therapy studies, which employs an efficient and rapid protocol for the introduction of exogenous genes.

Because the vector particles of the invention are highly efficient at transducing stem cells, they are particularly attractive for somatic gene therapy. Gene therapy can be used to treat any disorders characterized by a defect in a single gene, or which can be treated by producing expression of a gene, even though the cause of the disease is a multi-genic defect, or some non-genetic cause, such as an infection or autoimmunity. In particular, diseases that can be treated with the invention, in addition to those set forth in the background of the invention or that are obvious from the foregoing list of therapeutic genes, are hematopoietic disease, neural disease, joint-related disease, muscular disease, and liver disease. In particular, joint-related diseases include cells may be beneficial.

The present invention yet further discloses a method for monitoring the efficiency of the stem cell-mediated gene transfer based on detecting the presence of the genes (or the expression products) of the vector in various stem cell-derived lineages of the host. As disclosed in a specific embodiment, the presence of the genes of the vector can be monitored by any of the methods known in the art, but most preferably by PCR (using retroviral-specific primers) and/or by detecting the polypeptide product of the vector-encoded gene(s) (e.g., using immunochemical or fluorescence assays).

The disclosed novel highly efficient method of vector particle-mediated transduction of stem cells preferably comprises the steps of: (i) optionally inducing the proliferation of a target stem cell by pre-stimulation; and (ii) incubating the pre-stimulated target stem cell with a vector particle containing a gene of interest and pseudotyped with feline endogenous virus RD114 envelope protein. While traditionally, the transduced cells are expanded in culture, the present invention advantageously omits this step, and thus avoids inducing stem cell differentiation. In a less preferred embodiment, the target stem cell is pre-stimulated with cytokines and/or growth factors. These cytokines and growth factors can be selected from the group consisting of but not limited to: stem cell factor, Flt-3 ligand, interleukin-2, interleukin-3, interleukin-6, and phytohemagglutinin. According to the method of the instant invention, the optimal efficiency of retroviral-stimulated stem cell transduction requires using target cell density around $1-5 \times 10^4$ cells/cm$^2$ and is attained upon pre-stimulating target cells for 24–48 hours.

As pointed out above, the method of the present invention benefits from the use of RD114 pseudotyped retroviral vector particles substantially free of producer cells and producer cell supernatant. Such retroviral particles can be either pre-adsorbed on retronectin coated plates or concentrated by ultracentrifugation. As disclosed in a specific embodiment, HT1080-derived producer cells (and potentially other kinds of producer cells) contain in their medium an unidentified substance that induces phenotypic change in the target cells, leading to their elimination upon engraftment in the immunodeficient host. According to the method of the instant invention, retronectin-pre-adsorbed and ultrafiltration-concentrated retroviral particles and synthetic vector particles that contain RD114 binding polypeptides are free of contaminating and potentially harmful substances present in the culture media of producer cells, leading to the efficient transduction and engraftment of the target cells without any change in their phenotype. In a preferred embodiment, the disclosed method involves producing retronectin plates with pre-adsorbed retroviral vector particles as a part of a transduction kit which can be stored at low temperatures for long periods of time.

As exemplified in examples below, cells can be transduced by the vector particles of the invention by direct contact in tissue culture. For example, in a specific embodiment, cells are exposed to pre-loaded vector (adsorbed to surfaces) at 48 hours in culture. Alternatively, concentrated vector can be added to these cells. In yet another alternative, the cells at 48 hours in culture are contacted with pre-loaded vector, and concentrated vector is added at 72 hours. While this latter addition results in contact or exposure to producer cell supernatant, the total amount of supernatant is limited. This is because ultracentrifugation concentrates the virus 50 to 100-fold, although the concentrated virus is in approximately 50% solution of supernatant. Adding this to the media containing the target stem cells at a 10% volume means exposing the cells to 5% producer cell supernatant. Presumably, as a result of centrifugation, most of the adverse proteins do not concentrate due to their small size. Thus, the target stem cells are exposed to less than 10% of the concentrated producer cell fluid, which is likely to contain less than a proportional amount of unwanted proteins.

Pre-adsorbtion of Retroviral Vector Particles

As noted above, the retroviral particles can be pre-adsorbed onto a surface that promotes adherence of the retroviral particles. Optimal transduction using RD114-pseudotyped vectors of stem cells can be obtained by preloading/adsorption of vectors on surfaces, e.g., retronectin-coated culture dishes.

Suitable surfaces include, but are by no means limited to, plastic, glass, polymer particles (such as SEPHADEX and SEPHAROSE), gels, and the like. Preferred plastic surfaces are tissue culture vessels, flasks, or plates.

Preferably, the surface is coated with an adherence promoting agent. Such adherence promoting agents are typically biomolecules to which an RD114 pseudotyped virus adheres. Adherence can be detected by demonstrating the presence of more RD114 pseudotyped retroviral particles adhering to a surface in the presence relative to the absence of an adherence promoting agent. In specific embodiments, the adherence promoting agent is retronectin, fibronectin, or polylysine; retronectin is exemplified infra.

To adsorb the retroviral particles, retroviral particle-containing supernatant from a producer cell culture is contacted with the solid surface for a time and under conditions of temperature, pH, humidity, etc. that permit adsorbtion to occur. Once the particles are adsorbed, the supernatant can be decanted or otherwise removed. If desired, the adsorbed particles can be washed to remove additional impurities, e.g., proteins from the supernatant, although the washing step should be done under mild conditions so as not to remove the pre-adsorbed retroviral particles.

Pre-adsorbed Transduction Kits

Having shown that pre-adsorbtion of RD114 pseudotyped retroviral particles greatly increases transduction efficiency, it was further discovered that the pre-adsorbed particles could be stored for later use, thus permitting development of kits. Thus, the invention encompasses a service for producing high efficiency retroviral vector particles.

A kit of the invention comprises retroviral vector particles pseudotyped with feline endogenous virus RD114 envelope protein and containing a gene of interest their genome pre-adsorbed onto a surface that promotes adherence of the retroviral particles. As noted above, the retroviral vector particles are substantially free of producer cells and producer cell supernatant. Preferred kits employ plastic tissue culture containers (plates or vessels) as the surface to which the retroviral particles are adsorbed. The kits can be stored prior to use, preferably under conditions that preserve the transduction capability of the retrovirus particles, e.g., about 50%, preferably greater than about 75%, and more preferably greater than about 90% of the transduction potential of the retroviral particles at the time the kit is prepared. In a specific embodiment, the adsorbed particles are stored at −70° C. Experiments showed that the transduction efficiency was maintained after 48 hours of storage, one week of storage, and for longer periods under these conditions.

Accordingly, the invention provides a method for preparing such a kit. This method comprises contacting the surface with the retroviral vector particles for a sufficient period of time to permit adherence of the retroviral particles to the surface, and removing supernatant in which the retroviral particles were suspended from the surface. The surface can be washed.

Thus, a vector production service can be implemented, in which a gene of interest is provided by a customer to the service lab, who introduce it into an RD114-pseudotyped retroviral vector. The recombinant vectors are then adsorbed onto a suitable surface, e.g., a retronectin-coated tissue culture dish, and provided to the customer. The customer can use this kit, containing retroviral vectors that express the customer's gene of interest, to transduce stem cells.

Transduced Animal Models

Because of the high efficiency of transduction achieved by the present invention, it is possible to create animal models for human conditions by engrafting non-human animals with autologous or human stem cells transduced in accordance with the invention. Thus, the invention provides such non-human animals. Preferably, if the stem cells are human stem cells the animal is immunodeficient, so that it does not reject the engrafted cells. However, in pre-clinical studies, engraftment with autologous cells is desired. The present inventors have successfully engrafted monkeys with the same high level of efficiency found with immunodeficient mice.

The animal models can be used to study the fate of marker-gene containing transduced stem cells. Animal models in which the animals are engrafted with human stem cells can be used to study the effect of various pharmacological agents on the human cells, or to evaluate the effect of transgene production by the retroviral vectors on the animal physiology.

Suitable animals for these models include, but are by no means limited to, mice, rats, rabbits, hamsters, guinea pigs, and other rodents; dogs, cats, and other domesticated carnivores; sheep, goats, pigs, and other farm animals; and monkeys, chimpanzees, apes, and other primates.

In specific embodiments, the invention discloses a NOD/SCID murine model and an immunodeficient simian model. In one specific embodiment, the present invention discloses the use of RD114 pseudotyped oncoretroviral vector particles for transducing primitive human hematopoietic cells which are then injected into the bone marrow of NOD/SCID mice. According to this embodiment, the injected transduced stem cells repopulated host bone marrow with around 90% efficiency leading to the introduction of a transgene into various hematopoietic cell lineages. In yet another embodiment, RD114 pseudotyped retroviral particles are used to transduce monkey hematopoietic stem cells, which were then injected into a recipient monkey. According to this embodiment, the attained efficiency of engraftment is around 70%.

EXAMPLES

The invention may be better understood by reference to the following Examples, which is provided by way of exemplification and not limitation.

Example 1

Gene Transfer into Primitive Human Hematopoietic Cells Using Retroviral Vector Particles Pseudotyped with the Feline Endogenous Retrovirus (RD114) Envelope Protein Materials and Methods Cell lines and primary cell populations. Human hematopoietic cell lines (K562-ATCC CCL 243 and HEL-ATCC TIB 180), mouse fibroblasts (NIH3T3-ATCC CRL 1658), and human embryonic kidney cells (293T-ATCC CRL 1573) were grown in Dulbecco's Modified Eagles Medium (DMEM) supplemented with 10% Fetal Calf Serum (FCS). Human peripheral blood mononuclear cells (PBMC) were recovered from the blood of normal donors by centrifugation on Histopaque-1077 (Sigma). Human umbilical cord blood specimens were obtained from delivered placentas following uncomplicated births at a local delivery center. Mononuclear cell preparations were recovered by centrifugation on Histopaque-1077. The CD34$^+$ cells in the cord blood mononuclear cell specimens were purified using a CD34-specific magnetic cell selection system according to instructions provided by the manufacturer (Miltenyi Biotec, Bergisch Gladbach, Germany). CD34$^+$, CD38$^-$ cells were recovered from the CD34$^+$ enriched populations by labeling with anti-CD34 (clone MY10) and anti-CD38 (clone HB-7) monoclonal antibodies (Becton Dickinson, San Jose, Calif.) conjugated to fluorescein isothiocyanate (FITC) or phycoerythrin (PE), respectively, and sorted for the CD34$^+$, CD38$^-$ population using a vantage flow cytometer (Becton Dickinson).

Retroviral vector preparations. Vector particles pseudotyped with the feline endogenous virus (RD114) envelope protein were derived by generating producer cells from a packaging cell line designated FLYRD18 (Porter et al., Hum. Gene Ther., 1996, 7:913–919) Cossett, J. Virol., 1995, 69:7430; ECACC Accession No. 95091902. This packaging cell line had been derived from human sarcoma cells (HT1080) by introducing the gag-pol genes from murine leukemia virus (MuLV) and the env gene encoding the envelope protein of the RD114 virus. We derived producer cells from the FLYRD18 packaging cell line by introducing a vector genome (MGirL22Y) that encodes the enhanced green fluorescent protein (EGFP) and a drug resistant variant of human dihydrofolate reductase (L22Y) (Allay et al., Nat. Med., 1998, 4:1136–1143; Persons et al., Nat. Med., 1998, 4:1201–1205). The reading frames for these proteins are separated by an internal ribosomal entry site and transcribed into a bicistronic transcript under the control of the mouse stem cell virus (MSCV) long terminal repeat (LTR) (Cheng et al, Gene Therapy, 1997, 4:1013–1022). The transduced FLYRD114 cells were selected in trimetrexate or sorted for high EGFP expression as previously described (Allay et al., supra; Persons et al., supra). Individual clones were recovered by limiting dilution and their capacity for vector production was determined by assaying serial dilutions of conditioned medium on human HeLa cells and a high titer clone designated RD114/MGirL22Y was identified. This methodology was also used to obtain amphotropic producer cell populations, AM13/MGirL22Y and AM/MGirL22Y, generated from FLYA13 packaging cells (a derivative of HT1080; Cosset et al., 1995, J. Virol., 69:7430–7436) and PA317 packaging cells (Miller and Buttimore, 1986, Mol. Cell. Biol., 6:2895–2902) (ATTC Accession No. CRL 9078), respectively. GALV pseudotyped particles were generated by a producer clone derived from PG13 cells (Miller et al., 1991, J. Virol., 65:2220–2224) (ATCC Accession No. CRL 10686), and VSV-G pseudotyped particles were generated by a producer clone derived from 293T cells (Ory et al., 1996, Proc. Natl. Acad. Sci. USA, 93:11400–11406) using the techniques described above. Vector preparations were screened for replication-competent virus by a marker rescue assay using HeLa (ATCC Accession No. CCL 2) or K562 (ATCC Accession No. ATCC CCL 243) cells which contained an integrated vector genome encoding neomycin resistance (G1NA).

Vector particles pseudotyped with the RD114, VSV-G, or amphotropic envelope proteins were also generated in 293T cells which had been transfected with helper and vector plasmids (Persons et al., Blood Cells Mol. Dis., 1998, 24:167–182). For RD114 pseudotyped particles, the 293T cells were transfected with a plasmid containing the vector genome (pMGirL22Y), a second plasmid encoding the gag and pot proteins of MuLV (pEQPAM3-E), and a third plasmid encoding the env protein of RD114 feline endogenous retrovirus (pRDF). Between 48–72 hours following transfection, conditioned media was harvested, titered on HeLa cells and screened for replication-competent retrovirus by the marker rescue assay as described above.

In vitro analysis of gene transfer efficiency. All transductions were performed in medium which contained 6 mg/ml of polybrene. Various human and murine cell lines were transduced at specified multiplicities of infection (MOI) based on titers determined on HeLa cells. After an overnight incubation, the vector containing culture medium was removed and fresh medium was added. The cells were harvested 72 hours after transduction and analyzed for EGFP expression by flow cytometry (FACS caliber, Becton Dickinson, San Jose, Calif.).

Peripheral blood mononuclear cells (PBMC) (lymphocytes) were activated with phytohemagglutinin (PHA, 34 mg/ml) and interleukin-2 (IL-2, R&D Systems) at 100 U/ml for 48 hours in RPMI-1640 medium supplemented with 10% FCS for 48 hours prior to transduction. These activated human PBMC ($2 \times 10^4$/well) were then transduced in 48-well plates that had been coated with retronectin (CH-296, Takara Shuzo, Otsu, Japan) at a concentration of 20 mg/cm$^2$. Fresh medium containing IL-2 (100 U/ml) was used to replace the vector containing medium after overnight incubation and the cells were allowed to expand for 72 hours post-transduction before analysis by flow cytometry. Analysis showed that more than 95% of the cells reacted with an anti-CD3 specific monoclonal antibody (data not shown).

CD34$^+$ or CD34$^+$, CD38$^-$ purified primitive hematopoietic cell populations were cultured in Isccove's Modified Dulbecco's Medium (IMDM) plus 1% bovine serum albumin, human insulin (5 mg/ml), human transferrin (100 mg/ml), low density lipoproteins (10 mg/ml), 0.1 mM β-mercaptoethanol, stem cell factor (SCF, 300 ng/ml), Flt-3 ligand (300 ng/ml), interleukin-3 (IL-3, 10 ng/ml) and interleukin-6 (IL-6, 10 ng/ml). The cytokines were obtained from R&D Systems, Minneapolis, Minn. The cells were incubated for 24 hours at 37° C. in 5% CO$_2$ prior to transduction.

Transduction of the CD34$^+$ and CD34$^+$, CD38$^-$ cells was performed in retronectin coated 48-well plates ($1-2 \times 10^4$ cells per well at a concentration of $1-2 \times 10^5$ cells/ml). When indicated, the retronectin coated wells were pre-loaded with retroviral vector particles by placing 0.5 ml/cm$^2$ of medium conditioned by producer cells in each well and incubating for 20–30 minutes at room temperature. This medium was then aspirated and a serum-free culture medium (specified above) containing CD34$^+$ or CD34$^+$, CD38$^-$ purified cells was added. When transductions were performed without preloading, serum-containing medium (10% FCS) conditioned by producer cells was added to achieve the specified MOI in amounts up to 40% of the initial culture volume.

Gene transfer efficiency was analyzed by evaluating EGFP expression in transduced cells. After incubation, the CD34$^+$ or CD34$^+$, CD38$^-$ cells were washed in PBS containing 2% heat-inactivated FCS and then stained with mouse anti-CD38 (clone HB-7) and anti-CD34 (clone My10) monoclonal antibodies conjugated to PE or allophycocyanin (APC, Becton Dickinson, San Jose, Calif.), respectively, washed, and resuspended in PBS containing 2% FCS. Four color flow cytometry was performed and the data were analyzed using the Cell Quest Software Package (Becton Dickinson).

To assay gene transfer into clonogenic progenitors, transduced and control hematopoietic cells were replated after 96 hours of culture into Methocult GF (H4434, Stem Cell Technologies, Vancouver, B.C., Canada) which had been pretreated with 1.2 U/ml thymidine phosphorylase at 37° C. for two hours. Cultures were established with or without 100 nM trimetrexate. At this concentration of trimetrexate, no colonies were formed in the samples containing control (untransduced) cells. Hematopoietic cells were cultured in 35 mm plates (1 ml of medium per plate) at 37° C. in a 5% CO$_2$ humidified atmosphere for 10–15 days after which the colonies were enumerated.

Analysis of gene transfer into cells that establish human hematopoiesis in immunodeficient (NOD/SCID) mice. Purified CD34$^+$ cells were prestimulated in medium containing SCF, Flt-3 ligand, IL-3 and IL-6 as described above for 24 hours at a concentration of $1-2 \times 10^5$ cells/ml. The cells in this medium were then transferred to retronectin coated culture plates to which vector particles had been absorbed (pre-loaded) or to retronectin coated plates without virus. In the later case, vector particles were added in the form of conditioned medium (constituting up to 20% of the culture volume). All cultures were diluted 2-fold with serum-free medium containing cytokines at 48 hours and harvested for injection at 96 hours.

The NOD/SCID mice (Jackson Laboratories, Bar Harbor, Me.) were housed in sterile microisolator cages and supplied with sterile food, acidified water and bedding. These six- to eight-week-old mice were used after sublethal irradiation (3–5cGy-$^{127}$Cs source). Each mouse was injected with 1–1.5×10$^5$ freshly isolated CD34$^+$ cells (>95% purity) or after expansion of this input volume for up to 96 hours in culture. The mice were sacrificed 8–10 weeks following injection and bone marrow cells were harvested for flow cytometric analysis and in vitro culturing.

Bone marrow cells from animals injected with human cells was subjected to flow cytometric analysis using conjugated antibodies against human surface antigens as follows: 1) CD45-APC to screen human hematopoietic cells; 2) CD19-PE to screen B-lymphocytes; and 3) CD33-PE to screen myeloid cells. These antibodies were obtained from Pharmingen (San Diego, Calif.). 5–10×10$^5$ bone marrow cells were mixed with either rat anti-mouse CD16/CD32 Fc block (clone 2.4G2, Pharmingen) or 10% heat-inactivated pooled mouse serum (to block non-specific antibody binding), and then incubated with saturating amounts of one of the conjugated antibodies. Cells from each animal were also stained with appropriate conjugated, isotype matched, control antibodies obtained from Becton Dickinson or Pharmingen. After incubation, cells were resuspended in red cell lysis buffer and washed twice in PBS containing 2% FCS. In all experiments cells stained with the isotype control antibody were used to set the quadrant markers such that the negative quadrant contained at least 97% of the control cells. The percentage of engrafted human cells was determined by CD45 positivity, followed by the determination of lineage marker and EGFP expression in the CD45$^+$-gated population.

The number of total and trimetrexate-resistant human clonogenic progenitors was determined in aliquots of bone marrow cells as described above. After 10–14 days, individual colonies were plucked from the methylcellulose and processed to recover DNA. Specifically, after scoring the plates, 20 colonies (or less, if fewer were present) were picked at random and incubated in lysis buffer [50 nM Tris (pH 8.5), 1 mM EDTA, 0.5% Tween20, and 100 ug/ml proteinase K] at 56° C. for 2 hours. To inactivate the proteinase K, the samples were heated at 95° C. for 10 minutes. The DNA samples were assayed for EGFP coding sequences using the polymerase chain reaction (PCR) methodology. PCR was performed with PCR Core Kit (Boehringer Mannheim) according to the manufacturer's instructions. The amplification conditions were as follows: 92° C. for 2 min., then 35 cycles of 92° C. for 1 min., 60° C. for 1 min., and 72° C. for 1 min., followed by a final elongation step of 7 min. at 72° C. Primers which amplify a 829 base pair (bp) fragment of human alpha satellite DNA, 5'-AATTTCAGCTGACTAAACA-3' (SEQ ID NO:4) and 5'-TTTAGTTAGGTGCAGTTAT-3' (SEQ ID NO:2), were used to confirm the presence of human DNA in each sample. The PCR amplification of the EGFP gene was performed with the primers 5'-ACCCCGACCACATGAAGCAGC-3' (SEQ ID NO:3) and 5'-CGTTGGGGTCTTTGCTCAGGG-3' (SEQ ID NO:4), resulting in a 417 bp product. Primers specific to the β-actin gene, 5'-TGACGGGGTCACCCACACTGTGCCCATCTA-3' (SEQ ID NO:5) and 5'-CTAGAAGCATTTGCGGTGGACGATGGAGGG-3' (SEQ ID NO:6), were used as an internal control and gave a 604 bp product. The PCR products were electrophoresed on a 1% agarose gel with ethidium bromide staining to visualize DNA. Samples that failed to produce PCR fragments for either β-actin or alpha satellite DNA were not included in the calculation of gene transfer efficiency.

Results

Enhanced transduction of human hematopoietic stem cells with RD114 pseudotyped vector particles. The titer of infectious particles of various oncoviral vector preparations (i.e., RD114, amphotropic, GALV, and VSV-G pseudotyped vector particles containing MGirL22Y retroviral genome) was determined prior to transduction by limiting dilution on HeLa cells. Human cord blood CD34$^+$ cells were cultured for 24 hours in cytokine-containing, serum-free medium (see above) and then transduced on retronectin coated plates. Serum-containing (10% FCS), conditioned medium from producer cells was added in amounts necessary to achieve the specified MOIs (but not exceeding 40% of the culture volume). After 24 hours fresh, serum-free cytokine-containing medium was added in amounts equal to the culture volume (2×dilution), and, after an additional 48 hours, the cells were analyzed for EGFP expression. With a single exposure at MOI of 5, the RD114 pseudotyped particles were far more efficient at transducing human CD34$^+$ cells than were vector particles pseudotyped with the amphotropic, GALV, or VSV-G env proteins. Human T-lymphocytes activated by PHA and IL-2 and human leukemia cells (K562 and HEL) were also far more efficiently transduced with RD114 than with amphotropic pseudotyped particles.

Aliquots of cells transduced with either RD114 or amphotropic pseudotyped particles were replated in methylcellulose immediately following transduction (48 hours of culture) and incubated for an additional 10–15 days, and the resistance to trimetrexate was determined. The RD114 pseudotyped vector efficiently transduced CD34$^+$ cells and their progenitors at a very low MOI indicating the presence of the appropriate receptor and cycling of a significant proportion of the cell population. Amphotropic pseudotyped particles failed to efficiently transduce the same population even at increased particle concentrations, consistent with a block to transduction at the receptor level.

Medium conditioned by derivatives of the HT1080 cell line alters the immunophenotype of primitive human hematopoietic cells during transduction. The immunophenotype of purified CD34$^+$ and CD34$^+$, CD38$^-$ cells was routinely monitored following in vitro culture and transduction. After 96 hours in serum-free culture medium with high dose of cytokines, purified CD34$^+$, CD38$^-$ cells retained their phenotype (see also Bhatia et al., J. Exp. Med., 1997, 186:619–624). In contrast, the exposure of CD34$^+$, CD38$^-$ cells to the medium conditioned by the RD114/MGirL22Y producer cells during transduction caused the majority of CD34$^+$, CD38$^-$ cells to become CD38$^+$. While only a small decrease in total clonogenic progenitors accompanied this phenotypic change (p-NS), the inventors have found that CD34$^+$ cells exposed to conditioned medium from the RD114/MGirL22Y producer cells failed to engraft in murine NOD/SCID recipients (N=4). In the same experiment, control CD34$^+$ cells (cultured identically but without exposure to vector particles) exhibited multilineage engraftment.

The observed phenotypic changes during transduction and the loss of primitive, repopulating cells may be caused directly by the RD114 env protein or, alternatively, may arise due to the action of some other component within the medium conditioned by the RD114/MGirL22Y producer cells. The later possibility seems more likely in light of finding that the culture medium from an amphotropic producer cell population (derived from the same original cell line, HT1080, as the producer cells for RD114 pseudotyped particles; Sommerfelt et al., Virology, 1990, 176:58–69), induced a similar immunophenotypic change in CD34+, CD38− cells, i.e., differentiation to a CD38+ phenotype. In contrast, the culture medium from an amphotropic producer cell line of a different origin (i.e., derived from PA317 cells) did not affect the immunophenotype of the CD34+, CD38− cells. RD114 pseudotyped producer cells were also derived from 293T cells (see above). The culture medium from these cells had no effect on the immunophenotype of CD34+, CD38− cells indicating that the immunodifferentiating/eliminating substance is indeed HT1080 cell-specific.

Transduction of primitive human hematopoietic cells by RD114 pseudotyped vector particles which had been pre-loaded onto retronectin coated plates. To provide the proper conditions for engraftment of transduced hematopoietic stem cells in murine NOD/SCID recipients the inventors set to prevent the undesirable effect of HT1080 cell-specific substance inducing the immunophenotypic change of CD34+, CD38− cells and the elimination of repopulating cells. Two alternative approaches were chosen.

According to the first approach, vector particles used for transduction were concentrated (and the volume of the culture medium containing harmful substances was greatly reduced) by ultracentrifugation at 25,000 rpm for 90 minutes. Thus, in the experiment presented in the viral supernatant was concentrated 54-fold with highly efficient recovery of the particles (60%) without any loss of the transduction efficiency.

According to an alternative approach, retroviral vector particles were adsorbed or "pre-loaded" onto retronectin coated plates by a brief incubation with virus-conditioned medium (Williams, Ann. N.Y. Acad. Sci., 1999, 872:109–113). In this way the vector particles become concentrated on the retronectin allowing the conditioned medium (containing a phenotype-altering substance) to be removed and replaced by medium containing the target cell population. Using conditioned medium from the RD114/MGirL22Y producer cells, the RD114 pseudotyped particles were adsorbed onto retronectin and then used to transduce CD34+, CD38− cells. This experimental approach proved to eliminate the undesirable effect of the HT1080-derived culture medium as it maintained the immunophenotype of the CD34+, CD38− cells with preservation of transduction efficiency. Transduction efficiency of pre-adsorbed viral particles remains unchanged after incubation for 48 hours at 4° C. and upon long-term storage (greater than 1 week) at −70° C. Transduction efficiency of pre-adsorbed viral particles is cell concentration dependent with the optimal efficiency obtained at a concentration of $1–5 \times 10^4$ cells/cm2.

Further experiments using CD34+, CD38− cells were performed to determine the optimum period of prestimulation prior to the transfer of the target cell population to retronectin coated plates pre-loaded with RD114 pseudotyped particles (N=4). Significant transduction of clonogenic progenitors (as reflected by trimetrexate resistance) was achieved already after 24 hours of prestimulation (38±15%;). However, the maximal effect was seen only after 48 hours of prestimulation (73±12%;).

Transduction of human cells capable of establishing hematopoiesis in immunodeficient mice with RD114pseudotyped vector particles. Purified CD34+ cells which had been prestimulated for 24–48 hours in serum-free medium were transduced by a single exposure to RD114 vector particles pre-loaded onto retronectin coated plates. After a maximum of 96 hours of culturing, expanded cells derived from an input $1.0–1.5 \times 10^5$ cells were injected into NOD/SCID immunodeficient murine recipients. Control cells were either not exposed to retroviral vector particles or transduced with amphotropic vector particles under various conditions. Bone marrow cells of three animals were analyzed 8–10 weeks after they had received CD34+cells transduced with RD114 pseudotyped vector particles. In each animal, there was a substantial population of bone marrow cells which reacted with a human CD45-specific monoclonal antibody. Among these CD45+ cells, the EGFP-positive cells were found in both the human lymphoid (CD 19+) and the human myeloid (CD33+) cell populations and in all three animals.

Overall rates of human engraftment in the NOD/SCID murine recipients and the levels of EGFP expression were determined. EGFP-positive cells were found in very significant numbers only in animals which received RD114 transduced CD34+ cells. The observed decrease in engraftment efficiency of CD34+ cells transduced by the RD 114 pseudotyped vector after 24 hours of prestimulation (compared to untransduced CD34+ cells [p<0.05]) was ameliorated by longer prestimulation (48 hours) which also resulted in improved EGFP expression. In correlation with reports of others (Glimm et al., Blood, 1999, 94:2161–2168; Henneman et al., Exp. Hematol., 1999, 27:817–825), a 48 hour-long prestimulation of producer cells prior to transduction appears to be an optimal condition for maximal gene transfer into NOD/SCID repopulating cells. The efficiency of gene transfer into repopulating hematopoietic cells was also evaluated by PCR analysis of DNA recovered from expanded bone marrow cells of experimental animals. A high percentage of cell clones from animals that had received cells transduced with RD114 pseudotyped vector particles produced EGFP-specific PCR product (Table 1). Of interest is the fact that the transduction frequencies of secondary progenitors of the CD34+ cell population (Table 1) were comparable to those observed with primary progenitors.

TABLE 1

Repopulation of NOD/SCID Mice by Transduced Cord Blood CD34+ Cells: Analysis of Engraftment and Gene Transfer Efficiency

| | In Vitro Analysis | | In Vivo Analysis | | | |
|---|---|---|---|---|---|---|
| | | | | | Human Progenitors | |
| Experimental Group | % EGFP Expression | % TMTX-R Progenitors | % Human CD45+ (range) | % EGFP+ (range)[0] | Trimetrexate Resistent (%) | PCR+ Colonies (%) |
| Expanded CD34+ Cells | 0 | 0 | 13.5 ± 17% (2.18–54.5%) | 0% | 0/228 (0%) | 0/20 (0%) |

TABLE 1-continued

Repopulation of NOD/SCID Mice by Transduced Cord Blood CD34+ Cells:
Analysis of Engraftment and Gene Transfer Efficiency

| | In Vitro Analysis | | In Vivo Analysis | | | |
|---|---|---|---|---|---|---|
| | | | | | Human Progenitors | |
| Experimental Group | % EGFP Expression | % TMTX-R Progenitors | % Human CD45+ (range) | % EGFP+ (range)[o] | Trimetrexate Resistant (%) | PCR+ Colonies (%) |
| (N = 10)[+] AM/MGirL 22Y Transduced CD34+ Cells (N = 9)* | 18–34% | 6.5–8% | 15.6 ± 16% (1.0–53%) | 0.2 ± 0.1% (0–0.6%) | 0/118 (0%) | 0/50 (0%) |
| RD/MGirL2 2Y Preload Only @ 24 Hours (N = 9) | 75–87% | 58–75% | 3.5 ± 5%[a] (0.6–15.8%) | 20.0 ± 22%[b] (0.6–71%) | 24/106 (23%) | 30/61 (49%) |
| RD/MGirL2 2Y Preload Only @ 48 Hours (N = 6) | 50–69% | 45–66% | 8.7 ± 8% (1.7–23.5%) | 40.5 ± 40%[b] (1.8–92%) | 81/326 (25%) | 58/98 (59%) |

[a] $p < 0.05$ compared to controls recipients
[b] $p < 0.05$ compared to AM/MGirL22Y
[o] Percent EGFP Expression of Engrafted Human Mononuclear Cells
[+] N = Number of murine recipients of $1.0$–$1.5 \times 10^5$ cells that exhibited > 0.5% human CD45+ cells
*Transduction by preloading alone @ 24 hours (N = 3) or with the addition of conditioned medium containing vector particles added at 48, and 72 hours Discussion The results presented above demonstrate that murine oncoretroviral vector particles pseudotyped with the envelope protein of feline endogenous virus (RD114) are transduced into human primitive hematopoietic cell lines, the CD34+ and CD34+, CD38− cell populations from cord blood, and the progenitors found in these populations far more efficiently than tested amphotropic, GALV and VSV-G pseudotyped oncoviral particles used at equivalent multiplicities of infection.

The disclosed producer cells generating the RD114 pseudotyped vector particles were derived from human sarcoma cells (HT1080) which apparently generate a substance that induces immunodifferentiation and depletion of repopulating cells. The nature and identity of this substance(s) is unknown and represents an important subject for future investigation. The evidence presented herein indicates that the RD114 pseudotyped particles are not the source of the substance since the same immunodifferentiation effect was observed with amphotropic particles produced by a derivative of the HT1080 cell line and was not observed with RD114 particles produced by human 293T cells.

As disclosed herein, the undesired effects of this substance could largely be avoided by preloading the RD114 particles onto retronectin plates prior to transduction of hematopoietic cell populations (although some depletion of NOD/SCID cells was observed compared to controls (Table 1). The ultimate solution may therefore involve the derivation of a RD114 packaging cell line from another cell type, such as NIH 3T3 mouse fibroblast cells which are currently the main source of vector preparations used in clinical trials.

As described above, cells in the cord blood CD34+ population transduced with retronectin-adsorbed RD114 pseudotyped vector particles are capable of establishing human hematopoiesis in immunodeficient (NOD/SCID) mice as reflected by the presence of the proviral genome in as many as 90% of the myeloid and lymphoid cells in the bone marrow of the transplant recipients. These results are far superior to gene transfer obtained to date with any onco- or lentiviral system.

The frequency of genetically modified, secondary progenitors present in bone marrow 8–10 weeks following transplantation was approximately equivalent to the frequency of genetically modified primary progenitors in the transduced population used for transplantation of the immunodeficient mice. These results imply that the frequency of transduction of NOD/SCID repopulating cells was equal to the transduction frequency of progenitors which, in turn, was equivalent to the transduction of the entire CD34+ cell population. In this respect, the results obtained in transducing human cord blood cells with RD114 pseudotyped vector particles are comparable to those generally obtained in transducing murine hematopoietic cells with ecotropic vector particles (Allay et al., supra; Persons et al., supra). These results contrast with the general experience with amphotropic and GALV pseudotyped oncoretroviral vector particles in which the transduction frequency of more mature human CD34+ cells and progenitors exceeds that of repopulating cells (van Henn, et al., Blood, 1998, 92:4013–4022; Marandin et al., 1998, Hum. Gene Ther., 9:1497–1511; Schlitz et al., Blood, 1998, 92:3163–3171; Conneally et al., Blood, 1998, 91:3487–3493). Moreover, a higher frequency of transduction of human NOD/SCID repopulating cells was achieved with a single exposure to RD114 pseudotyped vector particles at a low MOI than with multiple exposures to amphotropic, GALV and VSV-G pseudotyped vector particles used at generally higher MOIs (see also van Henn, et al., supra; Conneally et al., supra; van Henn, et al., supra; Marandin et al., supra; Schlitz et al., supra; Henneman et al., supra; Rebel et al, Blood, 1999, 93:2217–2224; Evans et al., Hum. Gene Ther., 1999, 10:1479–1489). It can be therefore hypothesized that the neutral amino acid transporter which is used as a receptor for both RD114 and ecotropic pseudotyped particles (Albritton et al., J. Virol., 1993, 67:2091–2096; Rasko et al., Proc. Natl. Acad. Sci. USA, 1999, 96:2129–2134) is expressed at functionally higher levels on human primitive hematopoietic cells than is the phosphate transporter which serves as a receptor for amphotropic and GALV pseudotyped vector particles.

It has been reported that VSV-G pseudotyped lentiviral vector particles are superior to VSV-G pseudotyped oncoretroviral vector particles at transducing quiescent NOD/SCID repopulating cells (Miyoshi et al., Science, 1999, 283:682–686). As discussed above, VSV-G pseudotyped oncoretroviral vector particles transduce NOD/SCID repopulating cells relatively inefficiently (Rebel et al., supra) compared to the results obtained herein with RD114 pseudotyped vector particles. It can be inferred therefore that RD114 pseudotyped lentiviral vector particles may be even more superior than RD114 pseudotyped oncoviral vector particles at transducing primitive hematopoietic cells. Recent results from the inventors' laboratory suggest that the RD114 pseudotyped lentiviral vector particles can be generated.

Taken together, the disclosed data suggest that (i) increasing the transduction and repopulation frequency by pretreating the target cells with cytokines and by immobilizing the retroviral vector particles on retronectin plates, (ii) overcoming the limitation imposed by receptor density for vector particle entry with the RD114-specific envelope protein, and (iii) the use of lentiviral vector internal proteins to facilitate translocation of the preintegration complex through the nuclear membrane may result in highly consistent and efficient transduction and repopulation of human hematopoietic stem cells thereby making gene therapy applications highly feasible and predictably successful.

Example 2
Optimal Transduction Using RD114-Pseudotyped Vectors of Hematopoietic Stem Cells Requires Preloading/Adsorption of Vectors on Retronectin Coated Dishes and is Cell Concentration Dependent As disclosed in Example 1 (supra), use of the RD114-pseudotyped retroviral vector particles pre-adsorbed (pre-loaded) onto retronectin-coated plates improves efficiency of stem cell transduction and NOD/SCID mice engraftment. It is further disclosed in Example 1 that the use of retronectin coated plates can eliminate the effects of unidentified producer cell-derived factors on the target stem cell differentiation and survival during engraftment.

In light of the above, it is important to attain the maximal efficiency of transduction when using retronectin-coated plates. We hypothesized that the transduction efficiency of the retronectin-adsorbed particles will be dependent on their density on the plate. Indeed, we found that gene transfer efficiency was maximized using retronectin concentration greater than 12 $\mu g/cm^2$. We further hypothesized that the transduction efficiency of the retronectin-adsorbed particles will be dependent on cell contact and, therefore, on cell concentration. Indeed, CD34+ cells from cord blood (CB) were efficiently transduced by adsorbed RD114-pseudotyped murine retroviruses on retronectin coated dishes at a concentration of 1–5×10$^4$ cells per cm$^2$. Data were obtained from representative experiments of 2 cords. It has been repeated twice with peripheral blood CD34$^+$ cells with similar results.

Example 3
RD114-Pseudotyped Murine Retroviruses Adsorbed to Retronectin Coated Plates Maintain Transduction Efficiency of Hematopoietic Stem Cells After Long-Term Storage at −70° C./Dry Ice We evaluated the stability of RD114-pseudotyped retoviral particles. We found that retroviruses pseudotyped with the RD114 envelope protein have a longer half-life in solution as compared to amphotropic pseudotyped retroviruses. We hypothesized that this stability would also be seen in the vector particles pre-loaded to the retronectin coated plates. We used frozen aliquots of a high titered RD114-MGirL22Y supernatant for these experiment. Peripheral blood CD34$^+$ cells were transduced on 6 well plates prepared as follows: (i) pre-loaded and then frozen at 70° C. for 48 hours before thawing, (ii) pre-loaded and placed at 4° C. for 48 hours, (iii) pre-loaded and placed at 4° C. for 24 hours, or (iv) freshly pre-loaded with thawed supernatant. There was gradual loss of gene transfer efficiency using pre-loaded plates placed at 4° C. as compared to pre-loaded plates prepared fresh. However, significant gene transfer efficiency could be maintained using pre-loaded plates that were kept frozen. We have subsequently repeated these experiments twice using plates stored at −70° C. for greater than one week with similar results.

Example 4
RD114-Pseudotyped Murine Retroviruses Can be Concentrated by Ultracentrifugation with Preservation of Transduction Efficiency As disclosed in Example 1, to ensure the efficient retroviral-mediated gene transfer to stem cells, it is highly important to eliminate the effect of producer cell-derived factors on the target cell differentiation and survival during engraftment. Therefore, in parallel to developing the transduction protocols using viral particles pre-adsorbed on retronectin-coated plates (see Examples 1–3, supra), we separated the retroviral vector particles from the detrimental content of the producer cell culture media using ultracentrifugation.

The results show that RD114-pseudotyped vector particles can be collected in a concentrated form by ultracentrifugation at 25,000 rpm for 90 minutes at 4° C. In this experiment, the viral supernatant was concentrated 54-fold with 60% recovery of total particles.

The concentrated RD114 supernatant demonstrated greatly increased transduction efficiency when tested on HeLa cells. AZT was added to cells as a control to rule out pseudo-transduction. To determine the transduction efficiency, double color Facs analysis was performed using peripheral blood transduced at 48 hours with GFP-preloaded virus, GFP-pre-loaded virus plus concentrated yellow fluorescent protein (YFP) plus supernatant at 48 hours, GFP-pre-loaded virus at 48 hours plus concentrated YFP plus supernatant at 72 hours, and GFP-pre-loaded virus at 72 hours.

Example 5
RD114 Envelope Protein Pseudotyped Lentiviral Constructs Can Be Concentrated by Ultracentrifugation As discussed in Example 1 (supra), the development of lentiviral-based retroviral vector particles can greatly improve the efficiency of gene transfer to the non-dividing cells. We have therefore set to obtain RD114-pseudotyped lentiviral vector particles which can be used for transduction of various quiescent stem cells.

We have first prepared lentiviral vectors transiently using VSV-G pseudotyping and have observed, as have others (e.g., see Evans, et al., Hum. Gene Ther., 1999, 10:1479–1489), that these vectors can efficiently transduce CD34+,CD38-cells while oncoretroviral particles pseudotyped with VSV-G do not.

We then sought to determine whether the RD114 envelope can pseudotype lentiviruses. We used two different transient transfection protocols and simultaneously derived VSV-G pseudotyped lentiviral vectors as an internal control to show that the transfection protocols worked. Supernatants from producer cells were collected and viral titers were determined using HeLa cells. We found that we could indeed pseudotype lentiviruses with the RD114 envelope protein.

While in the first series of experiments the titer of the RD114 pseudotyped lentiviral preparation was low, viral transduction did occur. We have determined that the low titer was the result of the poor expression of the envelope protein in the chosen producer system. In light of this observation, we have subsequently derived RD114-pseudotyped lentiviral particles with a much higher titer using a stronger promoter to drive the expression of RD114 envelope protein.

In addition, we have demonstrated that the RD114-pseudotyped lentiviral vector particles can be concentrated (as described in Examples 1–4, supra) by pre-loading on retronectin-coated plates or by ultracentrifugation.

Example 6
Repopulation of Hematopoietic Lineages of Immunodeficient Rhesus Monkey by Cord Blood CD34+ Cells Transduced with RD114-pseudotyped Retroviral Vector Particles Pre-adsorbed on Retronectin-coated Plates Materials and Methods G-CSF/SCF mobilized rhesus monkey peripheral blood CD34+ cells were selected and purified as described by Donahue et al. (Blood, 2000, 95:445–452). These cells were pre-stimulated under serum-free conditions essentially as described in Example 1 for NOD/SCID-repopulating cells (supra), except that the cytokines were SCF (300 ng/ml), Flt-3 ligand (300 ng/ml), and interleukin-6 (50 ng/ml). Following 48 hour pre-stimulation, cells were placed on retronectin-coated plates pre-loaded with RD-114-pseudotyped retroviral vector particles (RD114-MGirL22Y; prepared and pre-loaded as described in Examples 1 and 2, respectively) along with fresh media and cytokines. Upon overnight incubation (72 hours total), cells were removed from the plates, pelletted by centrifugation, and resuspended again in fresh media supplemented with cytokines. Cell suspension was plated for the second time on fresh retronectin-coated plates pre-loaded with retroviral vector particles. Cells were harvested at 96 hours, washed with fresh media, and injected into immunodeficient rhesus monkeys.

Results

The efficiency of engraftment of CD34+ cells transduced with RD114 pseudotyped vector particles in the hematopoietic lineages of the recipient monkey (96E113) was analyzed 0–106 days post-injection by monitoring EGFP expression. The percentage of hematopoietic cells expressing EGFP reached the maximal levels 64 days after injection, with the highest frequency of engraftment observed in monocytes (up to 98%) and peripheral mononuclear lymphocytes (PMN) (up to 83%). Lymphocytes and platelets also showed increased levels of EGFP expression, although not at the same level as monocytes or PMNs. Also, platelets achieved maximal EGFP expression at day 78 post transplantation.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all values are approximate, and are provided for description.

All patents, applications, publications, test methods, literature, and other materials cited herein are hereby incorporated by reference.

What is claimed is:

1. A method for transducing hematopoietic stem cells with a vector particle containing a gene of interest, which method comprises contacting target hematopoietic stem cells with vector particles pseudotyped with feline endogenous virus RD114 envelope protein and containing a gene of interest, wherein the vector particles are substantially free of factors that induce hematopoietic stem cell differentiation by being free of producer cells and producer supernatant to the extent that the amount of these differentiation-inducing factors is too low to cause the hematopoietic stem cells to differentiate, proliferate, or die, and whereby the transduced hematopoietic stem cells are capable of expressing the gene of interest and repopulating cell lineages when transplanted into a host.

2. The method of claim 1, wherein the vector particle is a retroviral vector particle comprising a modified retroviral genome containing the gene of interest.

3. The method of claim 2, wherein the retroviral particles are pre-adsorbed onto a surface that promotes adherence of the retroviral particles.

4. The method of claim 3, wherein the surface is coated with an adherence promoting agent.

5. The method of claim 4, wherein the adherence promoting agent is retronectin.

6. The method of claim 2, wherein the retroviral particles are freed of producer cells and producer cell supernatant by ultracentrifugation.

7. The method of claim 2, wherein the retroviral particle is an oncoviral particle.

8. The method of claim 2 wherein the retroviral particle is a lentiviral particle.

9. The method of claim 1 wherein the target hematopoietic stem cells are pre-stimulated.

10. The method of claim 9, wherein the target hematopoietic stem cells are stimulated by treatment with signaling molecules selected from the group consisting of cytokines, growth factors and phytohemagglutinin.

11. The method of claim 1, wherein the target hematopoietic stem cells are obtained from the group selected from cord blood cells, mobilized peripheral blood cells, bone marrow cells, and liver.

12. The method of claim 11, wherein the target hematopoietic stem cells are selected from the group consisting of CD34+ cells and CD34+CD38-cells.

13. The method according to claim 2, wherein upon engraftment of the transduced hematopoietic stem cells contacted one time with the retroviral particles into a host, greater than 10% of the transduced cells express the gene of interest.

14. The method according to claim 13, wherein greater than about 40% of the transduced cells express the gene of interest.

* * * * *